(12) United States Patent
Park et al.

(10) Patent No.: US 11,913,015 B2
(45) Date of Patent: Feb. 27, 2024

(54) EMBRYONIC CELL CULTURES AND METHODS OF USING THE SAME

(71) Applicant: UNIVERSITY OF MARYLAND, COLLEGE PARK, College Park, MD (US)

(72) Inventors: Chi-Hun Park, Laurel, MD (US); Bhanu Prakash V. L. Telugu, Columbia, MD (US)

(73) Assignee: UNIVERSITY OF MARYLAND, COLLEGE PARK, College Park, MD (US)

(*) Notice: Subject to any disclaimer, the term of this patent is extended or adjusted under 35 U.S.C. 154(b) by 337 days.

(21) Appl. No.: 16/606,199

(22) PCT Filed: Apr. 17, 2018

(86) PCT No.: PCT/US2018/028041
§ 371 (c)(1),
(2) Date: Oct. 17, 2019

(87) PCT Pub. No.: WO2018/195129
PCT Pub. Date: Oct. 25, 2018

(65) Prior Publication Data
US 2021/0163992 A1 Jun. 3, 2021

Related U.S. Application Data

(60) Provisional application No. 62/486,325, filed on Apr. 17, 2017.

(51) Int. Cl.
*C12N 15/877* (2010.01)
*A01K 67/027* (2006.01)
*C12N 5/073* (2010.01)

(52) U.S. Cl.
CPC .......... *C12N 15/877* (2013.01); *A01K 67/027* (2013.01); *C12N 5/0605* (2013.01); *C12N 2510/00* (2013.01); *C12N 2830/008* (2013.01)

(58) Field of Classification Search
CPC .......................... C12N 15/877; C12N 5/0605; C12N 15/8778; A01K 2227/108
USPC ............................................. 800/21; 435/325
See application file for complete search history.

(56) References Cited

U.S. PATENT DOCUMENTS

| | | | |
|---|---|---|---|
| 7,625,758 B2 | 12/2009 | Berkelman | |
| 7,627,436 B2 | 12/2009 | Park et al. | |
| 7,732,139 B2 | 6/2010 | Choi et al. | |
| 7,790,370 B2 | 9/2010 | Abreu et al. | |
| 7,863,048 B2 | 1/2011 | Berkelman | |
| 8,187,811 B2 | 5/2012 | Eriksson et al. | |
| 8,697,359 B1 | 4/2014 | Zhang | |
| 2002/0081614 A1 | 6/2002 | Case et al. | |
| 2003/0021776 A1 | 1/2003 | Rebar et al. | |
| 2004/0107454 A1 | 6/2004 | Wheeler et al. | |
| 2006/0204969 A1 | 9/2006 | Hoffman et al. | |
| 2006/0246567 A1 | 11/2006 | Rebar et al. | |
| 2007/0269827 A1 | 11/2007 | Harley | |
| 2008/0182328 A1 | 7/2008 | Snyder et al. | |
| 2008/0182332 A1 | 7/2008 | Cai et al. | |
| 2010/0291048 A1 | 11/2010 | Holmes et al. | |
| 2010/0292211 A1 | 11/2010 | Lavedan | |
| 2010/0323442 A1 | 12/2010 | Baetge et al. | |
| 2011/0039918 A1 | 2/2011 | Verschoor et al. | |
| 2011/0104674 A1 | 5/2011 | Akil et al. | |
| 2011/0319288 A1 | 12/2011 | Wojcik et al. | |
| 2012/0136039 A1 | 5/2012 | Aronin et al. | |
| 2012/0309642 A1 | 12/2012 | Chen et al. | |
| 2013/0123484 A1 | 5/2013 | Liu et al. | |

FOREIGN PATENT DOCUMENTS

| | | |
|---|---|---|
| EP | 1594971 A2 | 11/2005 |
| EP | 1594972 A2 | 11/2005 |
| EP | 1594973 A1 | 11/2005 |
| EP | 2535424 A1 | 12/2012 |
| WO | WO-2001/023525 A2 | 4/2001 |
| WO | WO-2002/057308 A2 | 7/2002 |
| WO | WO-2003/012143 A1 | 2/2003 |
| WO | WO-2004/069994 A2 | 8/2004 |
| WO | WO-2004/069995 A2 | 8/2004 |
| WO | WO-2004/070042 A1 | 8/2004 |
| WO | WO-2006/023719 A2 | 3/2006 |
| WO | WO-2006/104370 A1 | 10/2006 |
| WO | WO-2009/112882 A1 | 9/2009 |
| WO | WO-2010/065550 A2 | 6/2010 |
| WO | WO-2011/017293 A2 | 2/2011 |

(Continued)

OTHER PUBLICATIONS

Singhal (2016, PNAS, 113:122-127).*
Yang (2011, Biology of Reproduction, 85:946-953).*
Kunath (2005, Development 132, 1649-1661).*
You (Mol. Cells, 2004, 18:261-268).*
Park (2021, Stem Cell Reports, 16:212-223).*
Lim (2008, Cell Stem Cell, 3:543-554).*
Zhang Int. J. Mol. Sci. 2021, 22, 12918.*
Nishimura (2017, Stems Cells and Development, 26:1111-1120).*
U.S. Appl. No. 62/486,325, filed Apr. 17, 2017, Chi-Hun Park.
PCT/US2018/028041, Apr. 17, 2018, University of Maryland at.

(Continued)

*Primary Examiner* — Valarie E Bertoglio
(74) *Attorney, Agent, or Firm* — Ballard Spahr LLP

(57) ABSTRACT

The invention provides a composition comprising an extra-embryonic endodermal (XEN) call and/or an embryonic fibroblast (EF) cell. The invention also provides a method of establishing a XEN cell line or a primary embryonic fibroblast (EF) cell line in vitro, the method comprising culturing a zygote or parthenote from a mammal for a time sufficient to produce one or more blastocysts; and culturing the one or more blastocysts on feeder cells in culture medium for a time sufficient to produce one or a plurality of XEN cells and/or one or a plurality of EF cells.

11 Claims, 10 Drawing Sheets
Specification includes a Sequence Listing.

(56) References Cited

FOREIGN PATENT DOCUMENTS

| WO | WO-2012/001613 A1 | 1/2012 |
|---|---|---|
| WO | WO-2012/074758 A1 | 6/2012 |
| WO | WO-2012/158986 A2 | 11/2012 |
| WO | WO-2013/141680 A1 | 9/2013 |
| WO | WO-2013/142578 A1 | 9/2013 |
| WO | WO-2013/176772 A1 | 11/2013 |
| WO | WO-2014/065596 A1 | 5/2014 |
| WO | WO-2014/089290 A1 | 6/2014 |
| WO | WO-2014/093622 A2 | 6/2014 |
| WO | WO-2014/093661 A2 | 6/2014 |
| WO | WO-2014/099750 A2 | 6/2014 |
| WO | WO-2014/131833 A1 | 9/2014 |
| WO | WO-2014/165825 A2 | 10/2014 |
| WO | WO-2015/022541 A1 | 2/2015 |
| WO | WO-2015/200805 A2 | 12/2015 |
| WO | WO-2018/195129 A1 | 10/2018 |

OTHER PUBLICATIONS

International Search Report and Written Opinion were dated Aug. 28, 2018 by the International Searching Authority for International Application No. PCT/US2018/028041, filed on Apr. 17, 2018 and published as WO 2018/195129 dated Oct. 25, 2018 (Applicant—University of Maryland, College Park) (17 Pages).
International Preliminary Report on Patentability was dated Oct. 22, 2019 by the International Searching Authority for International Application No. PCT/US2018/028041, filed on Apr. 17, 2018 and published as WO 2018/195129 dated Oct. 25, 2018 (Applicant—University of Maryland, College Park) (11 Pages).
Cong, L. et al. "Multiplex genome engineering using CRISPR/Cas systems", Science, 339(6121):819-23 (2013).
Ding, S. et al., "Efficient transposition of the *piggyBac* (*PB*) transposon in mammalian cells and mice", Cell; 122:473-483 (2005).
Gaj, et al. "ZFN, TALEN, and CRISPR/Cas-based methods for genome engineering", Trends in Biotechnology, 31(7):397-405 (2013).
Hwang, W. Y. et al. "Tips for Cell Engineering using Cas9-GFP CRISPR plasmids", Nat. Biotechnol., 31(3):227-9 (2013).
Jiang, W. et al. "CRISPR-assisted editing of bacterial genomes", Nat. Biotechnol., 31(3):233-9 (2013).
Jinek, M. et al. "A Programmable Dual-RNA-Guided DNA Endonuclease in Adaptive Bacterial Immunity", Science; 337(6096):816-21 (2012).
Lange, A. et al. "Classical Nuclear Localization Signals: Definition, Function, and Interaction with Importin α", J. Biol. Chem., 282(8):5101-05 (2007).
Lillico, S. G. et al., "Live pigs produced from genome edited zygotes", Scientific Reports; 3, 2847 (2013).
Lillico, S. G. et al., "Mammalian interspecies substitution of immune modulatory alleles by genome editing", Scientific Reports; 6, 21645 (2016).
Mali, P. et al. "RNA-Guided Human Genome Engineering via Cas9", Science; 339 (6121):823-6 (2013).
Park, K.-E. et al., "Generation of germline ablated male pigs by CRISPR/Cas9 editing of the *NANOS2* gene", Scientific Reports; 7, 40176 (2017).
Park, K.-E. et al., "Targeted gene knock-in by CRISPR/Cas ribonucleoproteins in porcine zygotes", Scientific Reports; 7, 42458 (2017).
Sapranauskas, R. et al. "The *Streptococcus thermophilus* CRISPR/Cas system provides immunity in *Escherichia coli*", Nucleic Acids Research; 39:9275-82 (2011).
Verma, L. M. et al., "Gene therapy—promises, problems and prospects", Nature; 389:239-242 (1997).
Wang, X. et al., "One-step generation of triple gene-targeted pigs using CRISPR/Cas9 system", Scientific Reports; 6, 20620 (2016).
Yang, Y. et al., "Genetically humanized pigs exclusively expressing human insulin are generated through custom endonuclease-mediated seamless engineering", J. Mol. Cell Biol., 8, 174-177 (2016).

\* cited by examiner

EMBRYONIC CELL CULTURES AND METHODS OF USING THE SAME

RELATED APPLICATIONS

This application is a U.S. National Phase Application filed under 35 U.S.C. § 371 from and claiming priority to International Patent Application No. PCT/US2018/028041, filed Apr. 17, 2018, which claims the benefit priority to U.S. Provisional Application No. 62/486,325, filed on Apr. 17, 2017. The content of these filed applications is hereby incorporated by reference in their entireties.

INCORPORATION OF THE SEQUENCE LISTING

The sequence listing submitted herewith as a text file named "36429_0020U2_Sequence_Listing", created on Oct. 17, 2019 and having a size of 8,192 bytes is herein incorporated by reference in its entirety pursuant to 37 C.F.R. § 1.52(e)(5).

BACKGROUND

In domestic pigs and other livestock species, the conventional means for generating genetically engineered animals is somatic cell nuclear transfer (SCNT) or cloning, where somatic cells (typically fetal fibroblasts) are modified to introduce the intended genetic modification and then used as nuclear donors for SCNT. However, the efficiency of somatic cell gene targeting is typically low and requires a laborious and time-consuming screening process. Correct recombination events are rare (1 in 106-107 cells), often monoallelic, and require a second round of targeting for generating homozygous/biallelic modifications. Additionally, extended culture and screening in vitro can result in significant reductions in cell viability, ultimately affecting overall cloning efficiency. An often overlooked and less often discussed difficulty is targeting certain loci that are within heterochromatin regions of the genome in somatic cells, requiring additional rounds of targeting or screening of multiple clonal lines. Although, live offspring have been generated using CRISPRs and SCNT, the difficulties in culturing primary somatic cells long enough to edit, clonally propagate, and screen for correct recombinants, coupled with the challenging task of using the somatic cells for nuclear transfer, makes the technique intractable for an average laboratory. In this regard, microinjection of CRISPR reagents directly into the embryos is a straightforward and preferred option. A few publications have already successfully demonstrated the generation of bi-allelic knock-out pigs by injection of editors into zygotes (Wang, X. et al., 2016, Scientific reports 6, 20620; Lillico, S. G. et al., 2013, Scientific reports 3, 2847; Yang, Y. et al., 2016,. J Mol Cell Biol 8, 174-177; Park, K. E. et al., 2017, Scientific reports 7, 40176). A recent report showed the successful introduction of point mutations by microinjection in pig zygotes using zinc finger nucleases (Lillico, S.G. et al., 2016, Scientific reports 6, 21645). Additionally, short DNA sequences (or transgenes) were knocked-in into target loci by microinjection into in vivo derived zygotes for generation of live offspring bearing targeted mutations (Park, K. E. et al., 2017, Scientific reports 7, 42458). The prevailing consensus is that the genome in early zygote is in an open conformation and is thus ideal for targeting most loci with relative ease. That said the use of microinjected zygotes also has limitations, chief among them are large number of donor animals required to retrieve in vivo derived embryos for embryo transfers, high degree of mosaicism, and lack of predictable efficiencies in generating a cohort of edited animals that are required of a study, making this a less than ideal situation.

SUMMARY OF THE INVENTION

The present disclosure also provides a composition comprising an isolated extraembryonic endodermal (XEN) cell and/or an isolated embryonic fibroblast (EF) cell. In certain embodiments, the isolated XEN cell and/or the isolated EF cell is from an in vitro zygote. In certain embodiments, the in vitro zygote is cultured from about 4 days to about 6 days. In certain embodiments, the isolated XEN cell and/or the isolated EF cell is an ovine, caprine, bovine or porcine cell line. In certain embodiments, the isolated XEN cell has one or a combination of phenotypes selected from the group consisting of: $CDX2^-$, $NANOG^-$, $SOX2^-$, $GATA4^+$, $FOXA2^+$, $GATA6^+$ and $SOX17^+$. In certain embodiments, the isolated XEN cell and/or the isolated EF cell comprises a genetic modification. In certain embodiments, the in vitro zygote comprises a genetic modification. In certain embodiments, the composition is free or substantially free of one or a combination of: (i) embryonic epiblastic cells; (ii) cells from a fetus of an animal; and (iii) trophoblastic cells.

The present disclosure also provides an oocyte comprising a heterologous nucleus from a genetically modified extraembryonic endodermal (XEN) cell or a genetically modified embryonic fibroblast (EF) cell. The present disclosure also provides an embryo derived from the oocyte. The present disclosure also provides an embryo comprising a nucleus isolated from a genetically modified extraembryonic endodermal (XEN) cell or a genetically modified embryonic fibroblast (EF) cell.

The present disclosure also provides a library comprising at least two different isolated cell lines, wherein the isolated cell line is a extraembryonic endodermal (XEN) cell or a embryonic fibroblast (EF) cell. In certain embodiments, each of the at least two different isolated cell lines has a different genetic modification.

The present disclosure also provides a method of establishing an extraembryonic endodermal (XEN) cell line or a primary embryonic fibroblast (EF) cell line in vitro, the method comprising: a) culturing a zygote or parthenote from a mammal for a time sufficient to produce one or more blastocysts; and b) culturing the one or more blastocysts on feeder cells in culture medium for a time sufficient to produce one or a plurality of XEN cells and/or one or a plurality of EF cells. In certain embodiments, the feeder cells are mitotically inactivated.

The present disclosure also provides a method of producing a genetically modified mammal, the method comprising: (a) contacting a gene-modifying amino acid sequence and/or gene-modifying nucleic acid sequence with one or a plurality of extraembryonic endodermal (XEN) cells and/or primary embryonic fibroblast (EF) cells for a time period sufficient to produce a genetic modification in a genome of the one or a plurality of XEN cells and/or EF cells. In some embodiments, the method further comprises the step of: culturing blastocysts from a zygote of a mammal on feeder cells in culture medium for a time period sufficient to produce one or a plurality of XEN cells and/or one or a plurality of primary EF cells before step (a). In some embodiments, the method further comprises the step of: screening the one or plurality of XEN cells and/or the one or plurality of EF cells for a genetic modification after step (a).

In some embodiments, the method further comprises the step of: isolating one or more nuclei from the one or plurality of XEN cells and/or EF cells and implanting the one or more nuclei into an oocyte of a mammal after the step of screening. In some embodiments, the method further comprises the steps of: (i) culturing the oocyte for a time period sufficient to produce a mammalian embryo; and (ii) implanting the embryo into a host mammal to produce a genetically modified animal. In some embodiments, the method further comprises further comprises: contacting a gene-modifying amino acid sequence and/or gene-modifying nucleic acid sequence with one or a plurality of embryos in culture. In some embodiments, the method further comprises the step of: (i) culturing one or a plurality of zygotes from a mammal for a time sufficient to produce a blastocyst of the mammal, wherein the step is performed before step (a).

The present disclosure also provides a method of producing a germline mutation in a mammal, the method comprising (a) contacting a gene-modifying amino acid sequence and/or gene-modifying nucleic acid sequence with one or a plurality of XEN cells and/or or EF cells. In some embodiments, the method further comprises the step of: culturing blastocysts from a zygote of a mammal on feeder cells in culture medium for a time period sufficient to produce one or a plurality of XEN cells and/or one or a plurality of primary EF cells before step (a). In some embodiments, the method further comprises the step of: screening the one or plurality of XEN cells and/or the one or plurality of EF cells for a genetic modification after step (a). In some embodiments, the method further comprises the steps of: isolating one or more nuclei from the one or plurality of XEN cells and/or EF cells and injecting the one or more nuclei into an oocyte of a mammal after the step of screening. In some embodiments, the method further comprises the step of: (i) culturing the oocyte for a time period sufficient to produce a mammalian embryo; and (ii) implanting the mammalian embryo into a host mammal to produce a genetically modified mammal comprising the genetic modification.

The present disclosure also provides a method of producing genetically modified XEN cells and/or genetically modified EF cells, the method comprising: a) contacting a gene-modifying amino acid sequence and/or gene-modifying nucleic acid sequence with one or a plurality of zygotes or parthenotes from a mammal in culture for a time period sufficient to produce a genetic modification in the one or a plurality of zygotes or parthenotes; b) culturing blastocysts from the genetically modified zygote or parthenote on feeder cells in culture medium for a time period sufficient to produce one or a plurality of XEN cells and/or one or a plurality of EF cells. In some embodiments, the method further comprises the step of screening the one or a plurality of XEN cells and/or one or a plurality of EF cells for the presence or absence of the genetic modification.

The present disclosure also provides a method for culturing a XEN cell or an EF cell from a zygote of a mammal comprising: (a) allowing a blastocyst from a zygote to adhere to a surface in a culture vessel; and (b) culturing the blastocyst in cell medium for a time period sufficient for one or more cells from the blastocyst to differentiate into a XEN cell and/or an EF cell. In certain embodiments, the blastocyst is not derived from fetal cells. In certain embodiments, the cell medium comprises one or more of the following components: high-glucose Dulbecco's modified Eagle medium (DMEM), ES-qualified fetal calf serum, L-glutamine, an antibiotic, Non-essential Amino Acid (NEAA) cell culture supplement, human leukemia inhibitory factor (LIF) and Basic fibroblast growth factor (bFGF). In certain embodiments, the mammal is a sheep, goat, cow or pig. In certain embodiments, the genetic modification is an insertion of a nucleic acid segment of about 10,000 to about 100,000 base pairs. In certain embodiments, the genetic modification is an insertion of a nucleic acid segment of about 10,000 to about 50,000 base pairs, about 10,000 to about 25,000 base pairs, about 10,000 to about 20,000 base pairs, or about 10,000 to about 15,000 base pairs. In certain embodiments, the genetic modification is an insertion of a nucleic acid segment of about 25 to about 200 base pairs. In certain embodiments, the genetic modification is an insertion of a nucleic acid segment of about 25 to about 150 base pairs, about 25 to about 100 base pairs, about 25 to about 75 base pairs, or about 25 to about 50 base pairs. In certain embodiments, the gene-modifying amino acid sequence comprises one or a combination of functional amino acid sequences selected from: a CRISPR enzyme, TAL nuclease, zinc finger nuclease, and a transposon. In certain embodiments, the isolated XEN cell and/or the isolated EF cell is frozen. In certain embodiments, the isolated XEN cell and/or the isolated EF cell is frozen in liquid nitrogen. In certain embodiments, the isolated XEN cell and/or the isolated EF cell is in culture for at least about 5 days. In certain embodiments, the isolated XEN cell and/or the isolated EF cell is passaged from about 3 to about 25 times.

The present disclosure also provides a method of producing genetically modified XEN cells and/or genetically modified EF cells, the method comprising: a) contacting a gene-modifying amino acid sequence and/or gene-modifying nucleic acid sequence with one or a plurality of XEN cells and/or one or a plurality of EF cells. In some embodiments, the method further comprises culturing the one or a plurality of XEN cells and/or one or a plurality of EF cells with a cell culture medium.

The present disclosure also provides a method of a genetic modification in one or plurality of XEN cells and/or EF cells comprising: detecting the absence or presence of a genetic modification in a XEN cell or an EF cell comprising the genetic modification by contacting the cell or cells with a probe specific for the genetic modification. In some embodiments, the method further comprises obtaining one or plurality of XEN cells and/or EF cells comprising a genetic modification. The present disclosure also provides a cell line of EF cells free or substantially free of trophoblasts and XEN cells. In certain embodiments, the EF cells comprise a phenotype selected from one or a combination of: NANOG$^-$, SOX2$^-$, CDX2$^-$, AFP$^-$, GATA4$^-$, GATA6$^-$, FOXA2$^-$, SALL4$^-$, PDGFRa$^+$, uPA$^+$, Vimentin$^+$, and GPC-1$^+$. In certain embodiments, the isolated EF cell comprises a phenotype selected from one or a combination of: NANOG$^-$, SOX2$^-$, CDX2$^-$, AFP , GATA4$^-$, GATA6$^-$, FOXA2$^-$, SALL4$^-$, PDGFRa$^+$, uPA$^+$, Vimentin$^+$, and GPC-1$^+$. In certain embodiments, the NEAA cell culture supplement comprises glycine, L-Alanine, L-Asparagine, L-Aspartic acid, L-Glutamic Acid, L-Proline and L-Serine.

DETAILED DESCRIPTION OF EMBODIMENTS

Figure 1:
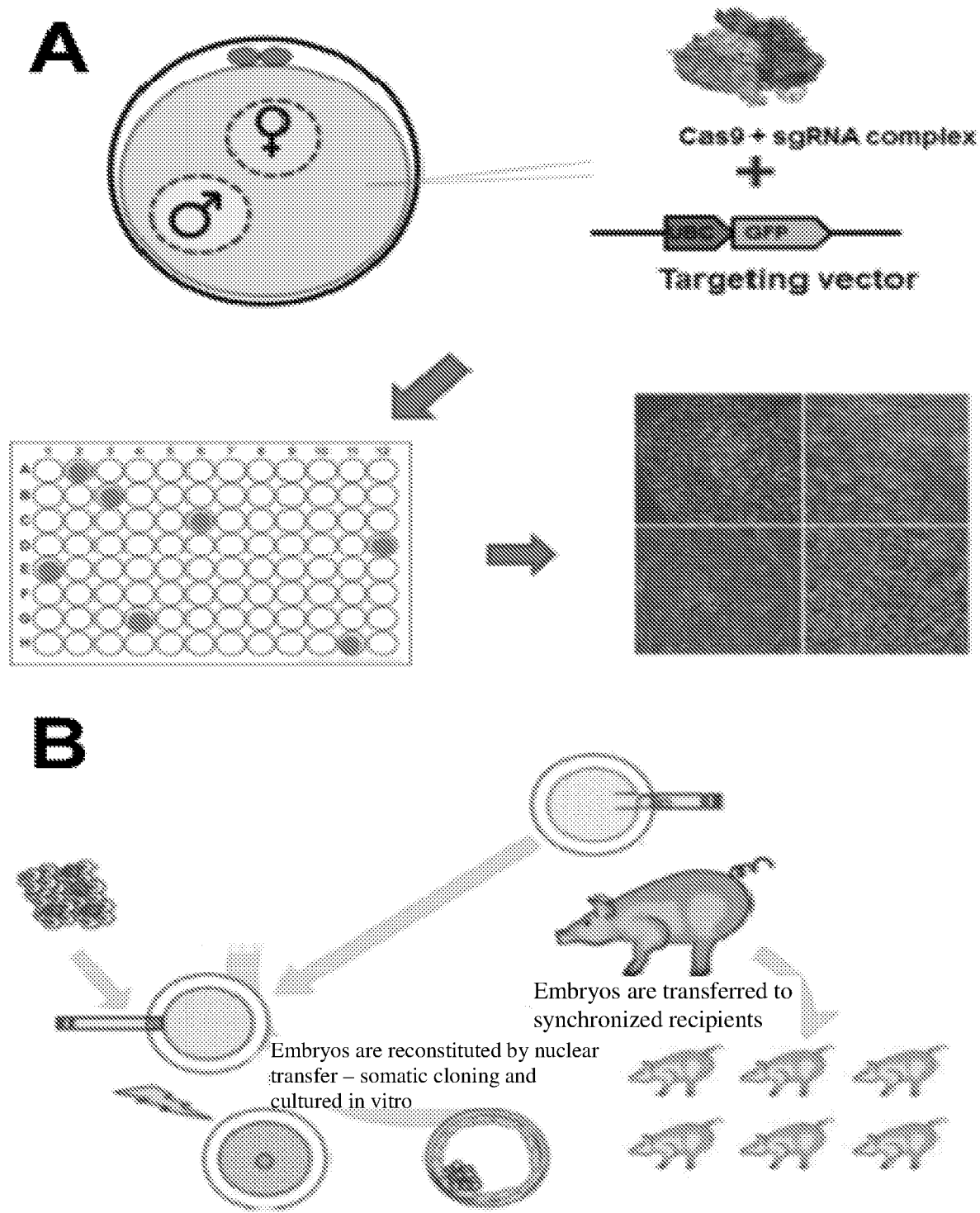
FIG. 1 shows a schematic outlining the embryo editing and nuclear transfer using primary embryonic edited lines as a means for high throughput generation of edited pigs. (A) Embryos (either in vitro or in vivo) are injected with a cocktail of CRISPR reagents (along with targeting reagents for knockin) to engineer desired genetic modification. The edited embryos are cultured to blastocyst stage and plated onto irradiated or mitotically inactivated mouse embryonic fibroblasts to establish primary outgrowths. The resultant clonal lines are screened for desired genetic modification, and used as donors in (B) nuclear transfer experiments to generate clonal lines of edited pigs.

Here, we developed an alternative method that utilizes the robustness of embryo injections, including the ease of access to target genes and high frequency of edits, with high predictability of establishing a cohort of genome edited animals, characteristic of somatic cell nuclear transfer (SCNT) (FIG. 1).

Briefly, in vitro or in vivo fertilized zygotes are microinjected for achieving targeted genetic modification, plated onto mitotically inactivated feeders to establish epiblast derived primary embryonic fibroblasts (EF) or extraembryonic endodermal (XEN) cells. The latter, which are the derivatives of the primitive endoderm can be maintained over extended periods of time (>40 passages) with no signs of senescence, prescreened for targeted modification and utilized to generate genome edited (GE) pigs with desired genetic modification.

With the ability to culture embryos, establish primary cells and screen for genotypes it is possible to perform genetic selection in vitro. In cattle and other livestock breeding systems, the genetic selection is primarily performed in male offspring, and the semen from the animals used for artificial insemination (AI) for rapid dissemination of genetics. That said, meiotic recombination during gametogenesis yields haplotypes (segments of genomes) that are inherited as a unit. Rare segregation events that result in optimal genome breeding value is often left to chance and the offspring after a prolonged gestation period will have to be screened to identify the right combination of haplotypes. By fertilizing oocytes and establishing embryos and primary cultures in vitro, the cells can be pre-screened, and the cells with optimal breeding value can be used for generating offspring. This will be of tremendous value to the livestock genetics industry. The ability to perform genome editing in embryos and prescreen for correct mutations in vitro prior to generating offspring will also be of tremendous value for the biomedical sector, where animals with particular mutations are often desired.

General Techniques and Selected Definitions

Unless specifically defined otherwise, all technical and scientific terms used herein shall be taken to have the same meaning as commonly understood by one of ordinary skill in the art (e.g., in cell culture, molecular genetics, recombinant DNA biology, transgenic animals, and biochemistry).

Unless otherwise indicated, the cell culture and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T.A. Brown (editor), Essential Molecular Biology: A Practical Approach, Volumes 1 and 2, IRL Press (1991), D.M. Glover and B.D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al., (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term about, unless stated to the contrary, refers to +/−10%, more preferably +1–5%, more preferably +/−2.5%, even more preferably +/−1%, of the designated value.

Non-Human Animals with a Targeted Germline Genetic Modification

The present invention relates to methods for producing a non-human animal, e.g. a sheep, goat, cow, pig or horse, comprising a targeted germline genetic modification. As used herein, the term "targeted germline genetic modification" refers to any genetic modification, such as but not limited to deletion, substation or insertion, made by way of human intervention at a predetermined location in the genome.

As used herein, a "genetically modified animal" refers to any animal in which one or more, preferably all, cells of the animal contains the targeted germline genetic modification.

In one embodiment, the genetic modification results in reduced expression of one or more genes and/or proteins in the animal and/or progeny thereof. Thus, in this embodiment, a gene knockout animal can be produced. As used herein, "reduced expression" of one or more genes and/or proteins is meant that the translation of a polypeptide and/or transcription of a gene in the cells of an animal produced using the methods of the invention, or progeny thereof, is reduced at least 10%, or at least 20%, or at least 30%, or at least 40%, or at least 50%, or at least 60%, or at least 70%, or at least 80%, or at least 90%, or at least 95%, or at least 98%, or at least 99%, or 100% relative to an isogenic animal lacking the genetic modification.

In an alternate embodiment, the genetic modification is the insertion of a transgene. The ability to target the transgene to a site of interest can be beneficial in that the transgene is interested at a site known or suspected to not cause any deleterious effects on the animal. The transgene may encode any functional protein or polynucleotide (such as an antisense polynucleotide or a dsRNA for RNAi). In some embodiments, the transgene encodes a protein which is expressed in the animal. In some embodiments, the transgene encodes a therapeutic protein such as an antibody.

In some embodiments, the transgene comprises one or more regulatory (promoter) elements operably linked to an open reading frame of interest (such as encoding a protein). "Operably linked" as used herein refers to a functional relationship between two or more nucleic acid (e.g., DNA) segments. Typically, it refers to the functional relationship of a transcriptional regulatory element to a transcribed sequence. For example, a promoter is operably linked to a coding sequence, such as an open reading frame encoding, if it stimulates the transcription of the coding sequence in an appropriate cell. Generally, promoter transcriptional regulatory elements that are operably linked to a transcribed sequence are physically contiguous to the transcribed sequence, i.e., they are cis-acting.

The transgene may also comprise a 3' non-translated sequence, for example from about 50 to 1,000 nucleotide base pairs, which may include a transcription termination sequence. A 3' non-translated sequence may contain a transcription termination signal which may or may not include a polyadenylation signal and any other regulatory signals capable of effecting mRNA processing.

"Addition of heterologous sequence" is meant to be any introduction of deoxyribonucleotide, nucleotide or DNA sequence within a gene, chromosome or genome of an organism. Also known as a "knock-in" which is meant an alteration in the nucleic acid sequence that replaces the endogenous, normal or wild-type allele with an exogenous allele. The exogenous allele includes but is not limited to a full length gene of the same or a different species, a section of a gene of the same or different species, a replacement cassette and reporter or selection genes and markers. Knock-in mutations can be produced by homologous recombination, site-specific deletion, repair mechanism provocation via targeting proteins, as well as site specific targeted DNA transposons. A "coding sequence" or a sequence "encoding" an expression product, such as a RNA, polypeptide, protein, or enzyme, is a nucleotide sequence that, when expressed or translated, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

In some embodiments, the targeted germline genetic modification is in a sex chromosome. In an alternate embodiment, the targeted germline genetic modification is a somatic chromosome. In some embodiments, all cells of the animal comprise the targeted germline genetic modification. Such animals produced using the methods of the present invention can readily be identified, and excluded from further breeding, using routine techniques such as PCR and/or DNA sequencing analysis of germline cells for the targeted genetic modification.

Animals produced using the methods of the invention can be screened for the presence of the targeted germline genetic modification. This can step can be performed using any suitable procedure known in the art. For instance, a nucleic acid sample, such as a genomic DNA sample, can be analyzed using standard DNA amplification and sequencing procedures to determine if the genetic modification is present at the targeted site (locus) in the genome. In some embodiments, the screening also determines whether the animal is homozygous or heterozygous for the genetic modification.

"Embryo" is a multicellular diploid eukaryote in early stage of development.

"Embryonic stem cell" or ES cell is a pluripotent cell derived from the inner mass of the blastocyst or early stage embryo.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed". An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "gene", also called a "structural gene," means a DNA sequence that codes for or corresponds to a particular sequence of amino acids which comprise all or part of one or more proteins or enzymes, and may or may not include introns and regulatory DNA sequences, such as promoter sequences, 5'-untranslated region, or 3'-untranslated region which affect for example the conditions under which the gene is expressed. Some genes, which are not structural genes, may be transcribed from DNA to RNA, but are not translated into an amino acid sequence. Other genes may function as regulators of structural genes or as regulators of DNA transcription.

"Gene of interest" refers to a nucleotide, nucleotide sequence, DNA, RNA, polypeptide, sequence on a chromosome or within the genome of an organism which is to be genetically modified or altered in some way. The gene of interest can be mutated or its nucleotide sequence may be altered.

"Genetic background" or "strain" refers to a genetic composition that is characteristic of an organism. Organisms that have been bred may have a known genetic strain that may be useful for different research reasons. Organisms that evolve in regions of the earth contain different genetic backgrounds which may alter gene function and important physiological functions.

"Genetic modification associated with the gene of interest" means a mutation or other genetic modification which corresponds to a gene that is being studied or selected for. The genetic modification may involve either endogenous or exogenous genes.

"Genetically modified" or "genetic modification" means a gene or other DNA sequence that is altered from its native state (e.g. by insertion mutation, deletion mutation, nucleic acid sequence mutation, or other mutation), or that a gene product is altered from its natural state (e.g. by delivery of a transgene that works in trans on a gene's encoded mRNA or protein, such as delivery of inhibitory RNA or delivery of a dominant negative transgene).

"Mutations" may produce organisms that are genetically modified or a specific genetic modification. "Mutations" may include but are not limited to one or more nucleic acid substitutions, deletions, frameshift mutations, or nonsense mutations.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature. A heterologous nucleus is a nucleus that has been transferred from another cell.

Any probes may be used in concert with any of the cells, compositions or methods disclosed herein. As used herein, the term "probe" refers to any molecule that may bind or associate, indirectly or directly, covalently or non-covalently, to any of the substrates and/or reaction products and/or encoded amino acid sequences disclosed herein that are heterologous as compared to the genome that they modify and whose association or binding is detectable using the methods disclosed herein. In some embodiments, the probe is a fluorogenic, fluorescent, or chemiluminescent probe, an antibody, or an absorbance-based probe. In some embodiments, an absorbance-based probe, for example the chromophore pNA (para-nitroanaline), may be used as a probe for detection and/or quantification of a nucleic acid sequence comprising a modification from an in vitro gene editing technique disclosed herein relative to a wild-type cell. In some embodiments, the probe may comprise an any molecule that may bind or associate, indirectly or directly, covalently or non-covalently, to a protein or peptide or chemical substance that is known to be present in unmodified cells and absent in modified cells, such that detecting an absence of a signal corresponds with the particular genetic modification being absent. Such is the case, in some embodiments, when trying to identify a knock-out type of genetic modification. A probe may be immobilized, adsorbed, or otherwise non-covalently bound to a solid surface, such that upon exposure to a XEN cell and/or an EF cell for a time period sufficient to perform an enzymatic reaction, it can be enzymatically cleaved. In some embodiments, cleavage of the substrate causes a biological change in the nature or chemical availability of one or more probes such that cleavage enables detection of the reaction product. For instance, if the step of detecting comprises use of FRET, cleavage of the substrate disclosed herein causes one of the chromophore to emit a fluorescent light under exposure to a wavelength sufficient to activate such a fluorescent molecule. The intensity, length, or amplitude of a wavelength emitted from fluorescent marker can be measured and is, in some embodiments, proportional to the presence, absence or quantity of enzyme present in the reaction vessel, thereby the quantity of enzyme can be determined from detection of the intensity of or fluorescence at a known wavelength of light.

An "activity-based probe," as used herein, refers to a certain embodiment of probe comprising a small molecule that binds to or has affinity for a molecule such as a substrate that binds an enzyme in the presence of such an enzyme, such that its bound or unbound state confers an activity readout to the enzyme. In some embodiments, the activity-based probe covalently or non-covalently binds to an enzyme or functional fragment herein. In some embodiments, the binding of the activity-based probe modifies the physical or biological activity of the enzyme. In some embodiments, the activity-based probe can be fluorescent or chemiluminescent. In some embodiments, the activity-based probe has a measurable activity of one value if the enzyme is inactive and another measurable activity if in an activated state. In some embodiments, any of the methods disclosed herein comprise a step of detecting the presence or absence of a genetic modification by exposing an activity-based probe to the surface of a XEN cell and/or an EF cell.

As used herein, the terms "fluorogenic" and "fluorescent" probe refer to any molecule (dye, quantum dot, peptide, or fluorescent marker) that emits a known and/or detectable wavelength of light upon exposure to a known wavelength of light. In some embodiments, the substrates or peptides with known cleavage sites recognizable by any of the enzymes expressed by one or a plurality of mucinous cysts are covalently or non-covalently attached to a fluorogenic probe. In some embodiments, the attachment of the fluorogenic probe to the substrate creates a chimeric molecule capable of a fluorescent emission or emissions upon exposure of the substrate to the enzyme and the known wavelength of light, such that exposure to the enzyme creates a reaction product which is quantifiable in the presence of a fluorimeter. In some embodiments, light from the fluorogenic probe is fully quenched upon exposure to the known wavelength of light before enzymatic cleavage of the substrate and the fluorogenic probe emits a known wavelength of light, the intensity of which is quantifiable by absorbance readings or intensity levels in the presence of a fluorimeter and after enzymatic cleavage of the substrate. In some embodiments, the fluorogenic probe is a coumarin-based dye or rhodamine-based dye with fluorescent emission spectra measureable or quantifiable in the presence of or exposure to a predetermined wavelength of light. In some embodiments, the fluorogenic probe comprises rhodamine. In some embodiments, the fluorogenic probe comprises rhodamine-100. Coumarin-based fluorogenic probes are known in the art, for example in U.S. Pat Nos. 7,625,758 and 7,863,048, which are herein incorporated by reference in their entireties. In some embodiments, the fluorogenic probes are a component to, covalently bound to, non-covalently bound to, intercalated with one or a plurality of markers from a genetic modification in the one or plurality of cells. In some embodiments, the fluorogenic probes are chosen from ACC or AMC. In some embodiments, the fluorogenic probe is a fluorescein molecule. In some embodiments, the fluorogenic probe is capable of emitting a resonance wave detectable and/or quantifiable by a fluorimeter after exposure to one or a plurality of enzymes disclosed herein. "Fluorescence microscopy," which uses the fluorescence to generate an image, may be used to detect the presence, absence, or quantity of a fluorescent probe. In some embodiments, fluorescence microscopy comprises measuring fluorescence resonance energy transfer (FRET) within a FRET-based assay.

A "chemiluminescent probe" refers to any molecule (dye, peptide, or chemiluminescent marker) that emits a known and/or detectable wavelength of light as the result of a chemical reaction. Chemiluminescence differs from fluorescence or phosphorescence in that the electronic excited state is the product of a chemical reaction rather than of the absorption of a photon. Non-limiting examples of chemiluminescent probes are luciferin and aequorin molecules. In some embodiments, a chemiluminescent molecule is covalently or non-covalently attached to a substrate disclosed herein or an enzyme, such that the excited electronic state can be quantified to determine directly that an enzyme, such as an aspartyl protease, is in a reaction vessel, or, indirectly, by quantifying the amount of reaction product was produced after activation of the probe on the substrate or a portion of the substrate.

The terms "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof.

Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after synthesis or polymerization, such as by conjugation with a labeling component.

The oligonucleotides of the disclosure also include those nucleic acid sequences disclosed herein that comprise nucleosides connected by charged linkages, and/or whose sequences are divided into at least two subsequences. In some embodiments, a first, second, and third subsequence or domains include a nucleotide binding domain (or DNA-binding domain), a Cas-binding domain, and a transcription terminator domain. In some embodiments, a first, second, and third subsequence or domains include a nucleotide binding domain, a Cas-binding domain, and a transcription terminator sequence, but, if any two domains are present the they must be oriented such that the nucleotide binding domain precedes the Cas-binding domain which, in turn precedes the transcription terminator domain in a 5' to 3' orientation. Any of the nucleosides within any of the domains may be 2'-substituted-nucleosides linked by a first type of linkage. The second subsequence includes nucleosides linked by a second type of linkage. In some embodiments, there exists a third subsequence whose nucleosides are selected from those selectable for the first subsequence, and the second subsequence is positioned between the first and the third subsequences. Such oligonucleotides of the disclosure are known as "chimeras," or "chimeric" or "gapped" oligonucleotides.

In the context of this disclosure, the term "oligonucleotide" also refers to a plurality of nucleotides joined together in a specific sequence from naturally and non-naturally occurring nucleobases. Nucleobases of the disclosure are joined through a sugar moiety via phosphorus linkages, and include any one or combination of adenine, guanine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine. The sugar moiety may be deoxyribose or ribose. The sugar moiety may be a modified deoxyribose or ribose with one or more modifications on the C1, C2, C3, C4, and/or C5 carbons. The oligonucleotides of the disclosure may also comprise modified nucleobases or nucleobases having other modifications consistent with the spirit of this disclosure, and in particular modifications that increase their nuclease resistance in order to facilitate their use as therapeutic, diagnostic or research reagents.

The terms "polypeptide", "peptide" and "protein" are used interchangeably herein to refer to polymers of amino acids of any length. The polymer may be linear or branched, it may comprise modified amino acids, and it may be interrupted by non-natural amino acids or chemical groups that are not amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, "more than one" or "two or more" 2, 3, 4, 5, 6, 7, 8, 9, or 10 or more. In some embodiments, "more than one" means 2, 3, 4, or 5 of the amino acids or nucleic acids or mutations described herein. In some embodiments, "more than one" means 2, 3, or 4 of the amino acids or nucleic acids or mutations described herein. In some embodiments, "more than one" means 2 or 3 of the amino acids or nucleic acids or mutations described herein. In some embodiments, "more than one" means 2 of the amino acids or nucleic acids or mutations described herein.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

The terms "biophysically effective amount" refers to an amount of nucleic acid in a system under physiological conditions (such as temperature, pH, exposure to percent oxygen, etc.) sufficient to produce a biological effect. In the case of embodiments drawn to the use of CRISPR, the biophysically effective amount refers to an amount of nucleic acid in a system under physiological conditions (such as temperature, pH, exposure to percent oxygen, etc.) sufficient to associate to or bind a Cas protein or functional fragment thereof in the presence of a Cas protein or functional fragment thereof. In some embodiments, the nucleic acid is a sgRNA, or a crRNA/tracr RNA duplex in a biophysically effective amount. In some embodiments, the Cas protein or functional fragment thereof is chosen from any of the sequences of Tables Y or functional fragments thereof.

"Cas binding domain" refers to a nucleic acid element or domain within a nucleic acid sequence or polynucleotide sequence that, in a biophysically effective amount, will bind or have an affinity for one or a plurality of proteins (or functional fragments thereof) encoded by one or a plurality of CRISPR-associated genes. In some embodiments, in the presence of a the one or a plurality of proteins (or functional fragments thereof) and a target sequence, the one or plurality of proteins and the nucleic acid element forms a biologically active CRISPR complex and/or can be enzymatically active on a target sequence. The terms "CRISPR-associated genes" refer to any nucleic acid that encodes a regulatory or expressible gene that regulates a component or encodes a component of the CRISPR system. In some embodiments, the terms "CRISPR-associated genes" refer to any nucleic acid sequence that encodes any of the proteins in Table Y (or functional fragments or variants thereof that are at least about 70, 75, 80, 85, 90, 95, 96, 97, 98, or 99% homologous to the sequences disclosed in either Table). In some embodiments, the terms "Cas-binding domain" or "Cas protein-binding domain" refers to a nucleic acid element or domain within a nucleic acid sequence or polynucleotide sequence that, in a biophysically effective amount, will bind to or have an affinity for one or a plurality of proteins in Table Y (or functional fragments or variants thereof that are at least about 70, 75, 80, 85, 90, 95, 96, 97, 98, or 99% homologous to the sequences disclosed in either Table). In some embodiments, the Cas binding domain consists of no more than about 10, 11, 12, 13, 14, 15, 16, 17 18, 19, 20, 25, 30, 35, 40, 41, 42, 43, 44, 45, 50, 60, 70, 80, 90, 100, 110, 120, 130, 140, 150, 160, 170, 180, 190, 200, 210, 220, 230, 240, 250 or more nucleotides in length and comprises at least one sequence that is capable of forming a hairpin or duplex that partially associates or binds to a biologically active CRISPR system at a concentration and within microenvironment suitable for CRISPR system formation. In some embodiments, the composition or pharmaceutical compositions comprises one or a combination of sgRNA, crRNA, and/or tracrRNA that consists of no more than about 25, 30, 35, 40, 45, 50, 60, 70, 80, 90, 100, 110, 120, 130, 140, 150, 160, 170, 180, 190, 200, 210, 220, 230, 240, 250 or more nucleotides in length and comprises at least one sequence that is capable of forming a hairpin or duplex that partially associates or binds to a biologically active amino acid sequence (or functional fragment disclosed herein) disclosed in Table Y at a concentration and within microenvironment suitable for CRISPR system formation and CRISPR enzymatic activity on a target sequence. In some embodiments, the Cas protein derived from the Cas9 family of Cas proteins or a functional fragment thereof.

The terms "transcription terminator domain" refers to a nucleic acid element or domain within a nucleic acid sequence (or polynucleotide sequence) that, in a biophysically effective amount, prevents bacterial transcription when the CRISPR complex is in a bacterial species and/or creates a secondary structure that stabilizes the association of the nucleic acid sequence to one or a plurality of Cas proteins (or functional fragments thereof) encoded by one or a plurality of CRISPR-associated genes such that, in the presence of the one or a plurality of proteins (or functional fragments thereof), the one or plurality of Cas proteins and the nucleic acid element forms a biologically active CRISPR complex and/or can be enzymatically active on a target sequence in the presence of such a target sequence and a DNA-binding domain. In some embodiments, the transcription terminator domain consists of no more than about 25, 30, 35, 40, 45, 50, 60, 70, 80, 90, 100, 110, 120, 130, 140, 150, 160, 170, 180, 190, 200, 210, 220, 230, 240, 250 or more nucleotides in length and comprises at least one sequence that is capable of forming a hairpin or duplex that partially drives association of the nucleic acid sequence (sgRNA, crRNA with tracrRNA, or other nucleic acid sequence) to a biologically active CRISPR complex at a concentration and microenvironment suitable for CRISPR complex formation.

The terms "DNA-binding domain" refer to an element or refers to a nucleic acid element or domain within a nucleic acid sequence or sgRNA that is complementary to a target sequence. In some embodiments, in a biophysically effective amount upstream from a Cas-binding domain, the DNA-binding domain will bind or have an affinity for one or a plurality of target nucleic acid sequences such that, in the presence of a biologically active CRISPR complex, one or plurality of Cas proteins can be enzymatically active on the target sequence. In some embodiments, the DNA binding domain consists of no more than about 20, 25, 30, 35, 40, 45, 50, 60, 70, 80, 90, 100, 110, 120, 130, 140, 150, 160, 170, 180, 190, 200, 210, 220, 230, 240, 250 or more nucleotides in length and comprises at least one sequence that is capable of forming Watson Crick basepairs with a target sequence as part of a biologically active CRISPR system at a concentration and microenvironment suitable for CRISPR system formation.

Genetic Modification Techniques
Transposons

In some embodiments, genetic modification is performed through the use of DNA transposons. Genetic modification of stem cells using DNA transposons is described, for example, in WO/2010/065550, which is incorporated by reference herein in its entirety. DNA transposons can be viewed as natural gene delivery vehicles that integrate into the host genome via a "cut-and-paste" mechanism. These mobile DNA elements encode a transposase flanked by inverted terminal repeats (ITRs) that contain the transposase binding sites necessary for transposition. Any gene of interest flanked by such ITRs can undergo transposition in the presence of the transposase supplied in trans. As noted, a "transposon" is a segment of DNA that can move (transpose) within the genome. A transposon may or may not encode the enzyme transposase, necessary to catalyze its relocation and/or duplication in the genome. Where a transposon does not code for its transposase enzyme, expression of said enzyme in trans may be required when carrying out the method of the invention in cells not expressing the relevant transposase itself. Furthermore, a transposon must contain sequences that are required for its mobilization, namely the terminal inverted repeats containing the binding sites for the transposase. The transposon may be derived from a bacterial or a eukaryotic transposon. Further, the transposon may be derived from a class I or class II transposon. Class II or DNA-mediated transposable elements are preferred for gene transfer applications, because transposition of these elements does not involve a reverse transcription step, which pertains to transposition of Class I or retro-elements and which can introduce undesired mutations into transgenes. For example, see Miller, A. D., RETROVIRUSES 843 (Cold Spring Harbor Laboratory Press, 1997), and Verma, L M. et al., Nature 389:239 (1997). Transposons also can be harnessed as vehicles for introducing "tagged" genetic mutations into genomes, which makes such genomic sites of transposon integration/mutation easy to clone and defined at the DNA sequence level. This fact makes transposon-based technology especially attractive in cultures of germline stem cells derived from a variety of species. For example, the first mutagenesis screens in mammals have established that the Sleeping Beauty transposon system can generate a high number of random mutations in both mouse and rat germinal cells in vivo. Alternatively, where mutagenic events can first be selected and then used to produce experimental animal models, random mutagenesis would be more feasible in tissue culture.

Similarly, transposons can be harnessed as vehicles for introducing mutations into genomes. Specifically, genes may be inactivated by transposon insertion. For example, such genes are then "tagged" by the transposable element, which can be used for subsequent cloning of the mutated allele. In addition to gene inactivation, a transposon may also introduce a transgene of interest into the genome if contained between its ITRs. Moreover, to insert or knockin a DNA construct or gene of interest into an existing site of transposition, stem cell lines or animals produced with transposons are designed to contain recognition sequences (e.g., pLox sties) within the transposon that act as substrates for DNA recombinase enzymes (e.g., Cre-recombinase). This would allow a gene of interest flanked by compatible recombinase recognition sequences to be delivered into the cells or animals in trans with a recombinase to catalyze integration of the gene of interest into the genomic locus of the transposon. The transposon may carry as well the regulatory elements necessary for the expression of the transgene, allowing for successful expression of the gene. Examples of transposon systems that can transpose in vertebrates have recently became available, such as Sleeping Beauty, piggyBac, Tol2 or Frog Prince. Each transposon system can be combined with any gene trap mechanism (for example: enhancer, promoter, polyA, or slice acceptor gene traps) to generate the mutated gene, as discussed below.

Sleeping Beauty (SB) and Frog Prince (FP) are TcI transposons, whereas piggyBac (PB) was the founder of the PB transposon family and Tol2 is a hAT transposon family member. Both the Sleeping Beauty and the Frog Prince transposon are found in vertebrates as inactive copies, from which active transposon systems have been engineered. The Tol2 transposon also has been found in vertebrates as an active transposon. The piggyBac transposon was originally found as an active transposon in insects but was subsequently shown to have high levels of activity in vertebrates, too, as shown in Ding S et al, Cell 122:473(2005). Each of these elements has their own advantages; for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore mutagenise overlapping, but distinct sets of genes. Therefore, to achieve the best possible coverage of genes, the use of more than one element is particularly preferred. In addition to naturally occurring transposons, modified transposon systems such as those disclosed in European patent documents EP1594973, EP 1594971, and EP1594972 also may be employed. In some embodiments, the transposons used possess highly elevated transpositional activity. In some embodiments, the transposon is a eukaryotic transposon, such as the Sleeping Beauty transposon, the Frog Prince transposon, the piggyBac transposon, or the Tol2 transposon, as discussed above.

The use of gene-trap constructs for insertional mutagenesis in tissue culture, where trapped events can easily be selected for, is advantageous over the random mutagenesis in animals. Gene trap vectors report both the insertion of the transposon into an expressed gene, and have a mutagenic effect by truncating the transcript through imposed splicing. Cells selected for a particular gene trap event can be used for the generation of animal models lacking this specific genetic function.

When transposons are used in insertional mutagenesis screens, transposon vectors typically constitute four major classes of constructs, suitable for identifying mutated genes rapidly. These contain a reporter gene, which should be expressed depending on the genetic context of the integration. Specific gene traps include, but are not limited to: (1) enhancer traps, (2) promoter traps, (3) polyA traps, and (4) splice acceptor traps. In enhancer traps, the expression of the reporter requires the presence of a genomic cis-regulator to act on an attenuated promoter within the integrated construct. Promoter traps contain no promoter at all. These vectors are only expressed if they land in-frame in an exon or close downstream to a promoter of an expressed gene. In polyA traps, the marker gene lacks a polyA signal, but contains a splice donor (SD) site. Thus, when integrating into an intron, a fusion transcript can be synthesized comprising the marker and the downstream exons of the trapped gene. Slice acceptor gene traps (or exon traps) also lack promoters, but are equipped with a splice acceptor (SA) preceding the marker gene. Reporter activation occurs if the vector is integrated into an expressed gene, and splicing between the reporter and an upstream exon takes place. The splice acceptor gene trap and polyA gene trap cassettes can be combined. In that case, the marker of the polyA trap part is amended with a promoter so that the vector also can trap downstream exons, and both upstream and downstream fusion transcripts of the trapped gene can be obtained. The foregoing constructs also offer the possibility to visualize spatial and temporal expression patterns of the mutated genes by using, e.g., LacZ or fluorescent proteins as a marker gene.

In some embodiments, the present invention relates to a method based on the combination of transposon-mediated insertional mutagenesis with a tissue culture system, e.g. culture of XEN cells or EF cells, which allows for the ready generation of in vitro XEN cell or EF cell libraries carrying a large number of different insertion events. Compared to classical nuclear transfer technologies and in vivo mutagenesis, moreover, this method is less costly and less labor-intensive, and it allows for the selection of the appropriate insertion(s) before establishing the corresponding animal models. Additionally, using these cells or libraries allows for establishment of a broader variety of animal models.

Libraries of XEN or EF cell lines can be generated by isolating and then pooling individual clonal lines with mutated genes. First, XEN or EF cell lines are genetically modified with a DNA construct that harbors a selectable marker, such as a gene encoding resistance to G418. Then, due to stable integration of the DNA construct into different locations within the genome, a mixed population of genetically distinct XEN or EF cell lines is selected using the selectable marker. By pooling these selected individual clonal lines with mutated genes, a library of mutant XEN or EF cell lines is generated.

The phrase "selectable marker" is employed here to denote a protein that enables the separation of cells expressing the marker from those that lack or do not express it. The selectable marker may be a fluorescent marker, for instance. Expression of the marker by cells having successfully integrated the transposon allows the isolation of these cells using methods such as, for example, FACS (fluorescent activated cell sorting). Alternatively, expression of a selectable marker may confer an advantageous property to the cell that allows survival of only those cells carrying the gene. For example, the marker protein may allow for the selection of the cell by conferring an antibiotic resistance to the cell. Consequently, when cells are cultured in medium containing said antibiotic, only cell clones expressing the marker protein that mediates antibiotic resistance are capable of propagating. By way of illustration, a suitable marker protein may confer resistance to antibiotics such as ampicillin, kanamycin, chloramphenicol, tetracycline, hygromycin, neomycin or methotrexate. Further examples of antibiotics are penicillins: ampicillin HCl, ampicillin Na, amoxycillin Na, carbenicillin disodium, penicillin G, cephalosporins, cefotaxim Na, cefalexin HCl, vancomycin, cycloserine. Other examples include bacteriostatic inhibitors such as: chloramphenicol, erythromycin, lincomycin, spectinomycin sulfate, clindamycin HCl, chlortetracycline HCl. Additional examples are marker proteins that allow selection with bactericidal inhibitors such as those affecting protein synthesis irreversibly causing cell death, for example aminoglycosides such as gentamycin, hygromycin B, kanamycin, neomycin, streptomycin, G418, tobramycin. Aminoglycosides can be inactivated by enzymes such as NPT II which phosphorylates 3'-OH present on kanamycin, thus inactivating this antibiotic. Some aminoglycoside modifying enzymes acetylate the compounds and block their entry in to the cell. Marker proteins that allow selection with nucleic acid metabolism inhibitors like rifampicin, mitomycin C, nalidixic acid, doxorubicin HCl, 5-flurouracil, 6-mercaptopurine, antimetabolites, miconazole, trimethoprim, methotrexate, metronidazole, sulfametoxazole are also examples for selectable markers.

In some embodiments, the present disclosure relates to methods of integrating an exogenous nucleic acid into the genome of at least one cell of an animal comprising administering directly to the cell: a) a transposon comprising the exogenous nucleic acid, wherein the exogenous nucleic acid is flanked by one or more inverted repeat sequences that are recognized by any of the aforementioned proteins; and b) any one of the aforementioned proteins to excise the exogenous nucleic acid from a plasmid, episome, or transgene and integrate the exogenous nucleic acid into the genome. Methods of genetically modifying cells of an animal using transposon are described, for example, in WO/2012/074758, which is incorporated by reference herein in its entirety. In some embodiments, the protein of b) is administered as a nucleic acid encoding the protein. In some embodiments, the transposon and nucleic acid encoding the protein of b) are present on separate vectors. In some embodiments, the transposon and nucleic acid encoding the protein of b) are present on the same vector. When present on the same vector, the portion of the vector encoding the hyperactive transposase is located outside the portion carrying the inserted nucleic acid. In other words, the transposase encoding region is located external to the region flanked by the inverted repeats. Put another way, the tranposase encoding region is positioned to the left of the left terminal inverted repeat or to the right of the right terminal inverted repeat. In the aforementioned methods, the hyperactive transposase protein recognizes the inverted repeats that flank an inserted nucleic acid, such as a nucleic acid that is to be inserted into a target cell genome.

In some embodiments, the organism is a livestock animal. In some embodiments the livestock animal is selected from the group consisting of a sheep, a goat, a cow, a pig and a horse.

The elements of the PiggyBac transposase system are administered to the cell in a manner such that they are introduced into a target cell under conditions sufficient for excision of the inverted repeat flanked nucleic acid from the vector carrying the transposon and subsequent integration of the excised nucleic acid into the genome of the target cell. As the transposon is introduced into the cell "under conditions sufficient for excision and integration to occur," the method can further include a step of ensuring that the requisite PiggyBac transposase activity is present in the target cell along with the introduced transposon. Depending on the structure of the transposon vector itself, such as whether or not the vector includes a region encoding a product having PiggyBac transposase activity, the method can further include introducing a second vector into the target cell that encodes the requisite transposase activity, where this step also includes an in vivo administration step.

The amount of vector nucleic acid comprising the transposon element, and in many embodiments the amount of vector nucleic acid encoding the transposase, which is introduced into the cell is sufficient to provide for the desired excision and insertion of the transposon nucleic acid into the target cell genome. As such, the amount of vector nucleic acid introduced should provide for a sufficient amount of transposase activity and a sufficient copy number of the nucleic acid that is desired to be inserted into the target cell. The amount of vector nucleic acid that is introduced into the target cell varies depending on the efficiency of the particular introduction protocol that is employed.

The particular dosage of each component of the system that is administered to the cell varies depending on the nature of the transposon nucleic acid, e.g. the nature of the expression module and gene, the nature of the vector on which the component elements are present, the nature of the delivery vehicle and the like. Dosages can readily be determined empirically by those of skill in the art.

Once the vector DNA has entered the target cell in combination with the requisite transposase, the nucleic acid region of the vector that is flanked by inverted repeats, i.e. the vector nucleic acid positioned between the PiggyBac transposase-recognized inverted repeats, is excised from the vector via the provided transposase and inserted into the genome of the targeted cell. As such, introduction of the vector DNA into the target cell is followed by subsequent transposase mediated excision and insertion of the exogenous nucleic acid carried by the vector into the genome of the targeted cell.

The subject methods may be used to integrate nucleic acids of various sizes into the target cell genome. Generally, the size of DNA that is inserted into a target cell genome using the subject methods ranges from about 0.5 kb to 100.0 kb, usually from about 1.0 kb to about 60.0 kb, or from about 1.0 kb to about 10.0 kb.

The subject methods result in stable integration of the nucleic acid into the target cell genome. By stable integration is meant that the nucleic acid remains present in the target cell genome for more than a transient period of time, and is passed on a part of the chromosomal genetic material to the progeny of the target cell. The subject methods of stable integration of nucleic acids into the genome of a target cell find use in a variety of applications in which the stable integration of a nucleic acid into a target cell genome is desired. Applications in which the subject vectors and methods find use include, for example, research applications, polypeptide synthesis applications and therapeutic applications. The hyperactive transposase can be delivered as DNA, RNA, or protein.

In some embodiments, the present disclosure relates to a colony of transgenic animals each such transgenic animal comprising one or more exogenous nucleic acid sequences and one or two internal tandem repeat sequences of the a transposon. The present disclosure also relates to one or more progeny from an animal comprising the one more more exogenous nucleic acid sequences and one or more internal tandem repeat sequences of the transposons. The present disclosure also relates to a colony of transgenic animals each such transgenic animal comprising one or more exogenous nucleic acid sequences and one or two internal tandem repeat sequences of the a transposon described herein. The present disclosure also relates to one or more progeny from an animal comprising the one or more exogenous nucleic acid sequences and one or more internal tandem repeat sequences of the transposons described herein.

The hyperactive PiggyBac transposase system described herein can be used for germline mutagenesis in a vertebrate species. One method would entail the production of transgenic animals by, for example, pronuclear injection of newly fertilized oocytes. Typically, two types of transgenes can be produced; one transgene provides expression of the transposase (a "driver" transgene) in germ cells (i.e., developing sperm or ova) and the other transgene (the "donor" transgene) comprises a transposon containing gene-disruptive sequences, such as a gene trap. The transposase may be directed to the germline via a ubiquitously active promoter, such as the ROSA26 (Gt(ROSA)26Sor), pPol2 (Polr2a), or CMV/beta-actin (CAG) promoters. Alternately, one may use a germline-restricted promoter, such as the spermatid-specific Protamine-1 (Prm1) promoter, for mutagenesis exclusively in developing sperm. In another embodiment, the germline specific promoter is a female-specific promoter (e.g., a ZP3 promoter).

Nucleases

XTN Nucleases

*Xanthomonas* TAL nucleases, referred to as XTNs from the bacterium *Xanthomonas*, bind DNA sequences in a site-specific manner as a mechanism to regulate their genes. Methods of using XTN nuclease for genetic modification of stem cells are described, for example, in WO/2012/158986, which is incorporated by reference herein in its entirety. XTNs can be modified in order to specifically bind to sites within the genome of many organisms. XTNs may be used to introduce targeted double-stranded or single-stranded breaks in the DNA, which can lead to small deletions at the site of the break during the Non-Homologous End Joining (NHEJ) process, thereby producing gene knockouts in cells and organisms. XTNs can also generate breaks in the DNA which can increase the frequency of exogenous sequence introduction by homologous recombination, thereby enabling specific gene editing (e.g. correction or mutation) or producing gene knock-ins in cells and organisms.

A central repeat domain containing multiple repeat units consisting of 33-35 amino acids determines nucleotide binding sites. Two essential adjacent amino acids known as repeat variable di-residue or RVDs are present in each repeat domain and separately specify a targeted base. The repeat domains and RVDs can be modified in order to target a gene or locus with high specificity (Mahfouz et a. (2011) PNAS 108,6,2623-2628). By fusing nuclease cleavage domains such as Fok1 to the XTNs, a nuclease is produced which is able to generate mutations in the genome of organisms in a site-specific manner. In one embodiment, XTNs are used to generate site specific mutations XEN cells, EF cells, zygotes or embryos. XTN DNA binding specificity depends on the number and order of repeats in the DNA binding domain. Repeats are generally composed of 34-35 amino acids. Nucleotide binding specificity is determined by the 12 and 13 amino acids, called the repeat variable diresidue (RVD), within the DNA binding domain repeats. The RVDs bind to one or more nucleotides and the code has been deciphered using arbitrary RVDs as follows: asaparagine/isoleucine (NI)=A; histidine/aspartic acid (HD)=C; asparagine/glycine (NG)=T; asparagines/asparagines (NN)=A, G; asparagines/serine (NS)=A, C, G and T. Since the RVD binding code is deciphered, natural or codon-optimized versions of natural XTNs can be used as a scaffold to generate sequence specific DNA binding XTNs. The repeats and RVDs in the DNA binding domains of XTNs may be modified and synthesized to generate site specific DNA binding XTNs. The DNA cleavage domain of nucleases are fused into the XTN to produce a hybrid XTN which binds to a specific site on the DNA and produces mutations.

Genetic modification of SSCs using XTNs requires undifferentiated SSCs, transfection of the SSCs with XTNs and a selection marker, clonal selection of genetically modified SSCs, germline transmission of genetically modified SSCs, and germline transmission of recipient founders.

the methods used in the present invention are comprised of a combination of genetic introduction methods, site-specific genetic modification or mutagenesis mechanisms of stem cells, and generation of site-specific genetically modified organisms from the stem cells. For all genetic modification or mutagenesis mechanisms one or more introduction and delivery method may be employed. The invention may include but is not limited to the methods described below.

In some embodiments, the site-specific genetic modification is produced in a stem cell, e.g. a zygote, embryo, XEN cell or EF cell. These stem cells can proliferate as cultured cells and be genetically modified without affecting their ability to differentiate into other cell types, including germ line cells. Generating site-specific mutations in stem cells, which can then be used to produce a genetically modified organism, first involves the design and development of a protein such as a XTN whose DNA binding domain is engineered for a specific target site within the genome. A protein consisting of both a DNA binding domain and a cleavage or insertional mutagenesis domain is developed.

In one embodiment of the invention, a site-specific mutagenesis technology is expressed in stem cells generating site-specific mutations. The binding domains of the site-specific mutagenesis technologies are modified to bind a particular location in the genome. The site-specific mutagenesis technology may be introduced into stem cells via transfection using lipofetamine. A transfection mixture may be prepared by mixing transfectamine with the site specific mutagenesis technology XTNs. After harvesting undifferentiated stem cells, one may then add transfection mixture to the cell suspension, incubate, wash and plate the stem cells onto fresh EF feeder layers.

Screening for XTN mediated site specific modification such as knockout mutations via NHEJ or knockin mutations using homologous recombination (HR) is done by selection with co-transfected vectors. SSCs are co-transfected with a XTN and a selection marker vector such as a fluorescent marker or antibody resistance within a lipid-based transfection reagent, lug total DNA is transfected with a ratio of 500 ng XTN to 500 ng selection vector. Clones are isolated and propagated to sufficient numbers to isolate DNA for screening and sequencing.

Zinc Finger Nucleases

The nuclease agent employed in the various methods and compositions disclosed herein can further comprise a zinc-finger nuclease (ZFN). Methods of genetically modifying stem cells with ZFNs are described, for example, in WO2015200805, which is incorporated by reference herein in its entirety. In one embodiment, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In one embodiment, the independent endonuclease is a Fok1 endonuclease. In one embodiment, the nuclease agent comprises a first ZFN and a second ZFN, wherein each of the first ZFN and the second ZFN is operably linked to a Fok1 nuclease subunit, wherein the first and the second ZFN recognize two contiguous target DNA sequences in each strand of the target DNA sequence separated by about 5-7 bp spacer, and wherein the Fok1 nuclease subunits dimerize to create an active nuclease to make a double strand break. See, for example, US20060246567; US20080182332; US20020081614; US20030021776; WO/2002/057308A2; US20130123484; US20100291048; WO/2011/017293A2; and Gaj et al. (2013) Trends in Biotechnology, 31(7):397-405 each of which is herein incorporated by reference.

CRISPR/Cas

The nuclease agent employed in the various methods and compositions can also comprise a CRISPR/Cas system. Methods of genetically modifying stem cells with the CRISPR/Cas system are described, for example, in WO2015200805, which is incorporated by reference herein in its entirety. Such systems can employ a Cas9 nuclease, which in some instances, is codon-optimized for the desired cell type in which it is to be expressed. The system further employs a fused crRNA-tracrRNA construct that functions with the codon-optimized Cas9. This single RNA is often referred to as a guide RNA or gRNA. Within a gRNA, the crRNA portion is identified as the "target sequence' for the givers recognition site and the tracrRNA is often referred to as the 'scaffold'. This system has been shown to function in a variety of eukaryotic and prokaryotic cells. Briefly, a short DNA fragment containing the target sequence is inserted into a guide RNA expression plasmid. The gRNA expression plasmid comprises the target sequence (in some embodiments around 20 nucleotides), a form of the tracrRNA sequence (the scaffold) as well as a suitable promoter that is active in the cell and necessary elements for proper processing in eukaryotic cells. Many of the systems rely on custom, complementary oligos that are annealed to form a double stranded DNA and then cloned into the gRNA expression plasmid. The gRNA expression cassette and the Cas9 expression cassette are then introduced into the cell. See, for example, Mali P et al. (2013) Science 2013 Feb. 15; 339 (6121):823-6; Jinek M et al. Science 2012 Aug. 17; 337 (6096):816-21 ; Hwang W Y et al. Nat Biotechnol 2013 March; 31(3):227-9; Jiang W et al. Nat Biotechnol 2013 March; 31(3):233-9; and, Cong Let al. Science 2013 Feb. 15; 339(6121):819-23, each of which is herein incorporated by reference.

The methods and compositions disclosed herein can utilize Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of, or directing the activity of, Cas genes. A CRISPR/Cas system can be a type I, a type II, or a type III system. The methods and compositions disclosed herein employ CRISPR/Cas systems by utilizing CRISPR complexes (comprising a guide RNA (gRNA) complexed with a Cas protein) for site-directed cleavage of nucleic acids.

Some CRISPR/Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together.

(i) A. Cas RNA-Guided Endonucleases

Cas proteins generally comprise at least one RNA recognition or binding domain. Such domains can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage. Cleavage includes the breakage of the covalent bonds of a nucleic acid molecule. Cleavage can produce blunt ends or staggered ends, and it can be single-stranded or double-stranded. Examples of Cas proteins include Cas1, Cas1B, Cas2, Cas3, Cas4, Cas5, Cas5e (CasD), Cas6, Cas6e, Cas6f, Cas7, Cas8a1 , Cas8a2, Cas8b, Cas8c, Cas9 (Csn1 or Csx12), Cas1O, Cas1Od, CasF, CasG, CasH, Csy1, Csy2, Csy3, Cse1 (CasA), Cse2

(CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx1O, Csx16, CsaX, Csx3, Csx1, Csx15, Csf1, Csf2, Csf3, Csf4, and Cul966, and homologs or modified versions thereof.

Cas proteins can be from a type II CRISPR/Cas system. For example, the Cas protein can be a Cas9 protein or be derived from a Cas9 protein. Cas9 proteins typically share four key motifs with a conserved architecture. Motifs 1, 2, and 4 are RuvC-like motifs, and motif 3 is an HNH motif. The Cas9 protein can be from, for example, *Streptococcus pyogenes, Streptococcus thermophilus, Streptococcus* sp., *Staphylococcus aureus, Nocardiopsis dassonvillei, Streptomyces pristinae spiralis, Streptomyces viridochromo* genes, *Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina*. Additional examples of the Cas9 family members are described in WO 2014/131833, herein incorporated by reference in its entirety. Cas9 protein from *S. pyogenes* or derived therefrom is a preferred enzyme. Cas9 protein from *S. pyogenes* is assigned SwissProt accession number Q99ZW2.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Some Cas proteins comprise at least two nuclease domains, such as DNase domains. For example, a Cas9 protein can comprise a RuvC-like nuclease domain and an HNH-like nuclease domain. The RuvC and HNH domains can each cut a different strand of double-stranded DNA to make a double-stranded break in the DNA. See, e.g., Jinek et al. (2012) Science 337:816-821, hereby incorporated by reference in its entirety.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single-strand break at a CRISPR RNA recognition sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA. An example of a mutation that converts Cas9 into a nickase is a D10A (aspartate to alanine at position 10 of Cas9) mutation in the RuvC domain of Cas9 from S. pyogenes. Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) Nucleic Acids Research 39:9275-9282 and WO 2013/141680, each of which is herein incorporated by reference in its entirety. Such mutations can be generated using methods such as site-directed mutagenesis, PCR-mediated mutagenesis, or total gene synthesis. Examples of other mutations creating nickases can be found, for example, in WO/2013/176772A1 and WO/2013/142578A1, each of which is herein incorporated by reference.

Cas proteins can also be fusion proteins. For example, a Cas protein can be fused to a cleavage domain, an epigenetic modification domain, a transcriptional activation domain, or a transcriptional repressor domain. See WO 2014/089290, incorporated herein by reference in its entirety. Cas proteins can also be fused to a heterologous polypeptide providing increased or decreased stability. The fused domain or heterologous polypeptide can be located at the N-terminus, the C-terminus, or internally within the Cas protein.

A Cas protein can be fused to a heterologous polypeptide that provides for subcellular localization. Such heterologous peptides include, for example, a nuclear localization signal (NLS) such as the SV40 NLS for targeting to the nucleus, a mitochondrial localization signal for targeting to the mitochondria, an ER retention signal, and the like. See, e.g., Lange et al. (2007) /. Biol. Chem. 282:5101-5105. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also be linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, for example, WO 2014/089290, herein incorporated by reference in its entirety. The cell-penetrating domain can be located at the N-terminus, the C-terminus, or anywhere within the Cas protein. Cas proteins can also comprise a heterologous polypeptide for ease of tracking or purification, such as a fluorescent protein, a purification tag, or an epitope tag. Examples of fluorescent proteins include green fluorescent proteins (e.g., GFP, GFP- 2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalamal, GFPuv, Sapphire, T-sapphire), cyan fluorescent proteins (e.g. eCFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611 , mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, SI, T7, V5, VSV-G, histidine (His), biotin carboxyl carrier protein (BCCP), and calmodulin.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g. , a Cas gene) and which can transfer such a nucleic acid sequence of interest to a target cell.

(ii) B. Guide RNAs (gRN As)

A "guide RNA" or "gRNA" includes an RNA molecule that binds to a Cas protein and targets the Cas protein to a specific location within a target DNA. Guide RNAs can comprise two segments: a "DNA-targeting segment" and a "protein-binding segment." "Segment" includes a segment, section, or region of a molecule, such as a contiguous stretch of nucleotides in an RNA. Some gRNAs comprise two separate RNA molecules: an "activator-RNA" and a "targeter-RNA." Other gRNAs are a single RNA molecule (single RNA polynucleotide), which can also be called a "single-molecule gRNA," a "single-guide RNA," or an "sgRNA." See, e.g., WO/2013/176772A1, WO/2014/065596A1, WO/2014/089290A1, WO/2014/093622A2, WO/2014/099750A2, WO/2013142578A1, and WO 2014/131833A1, each of which is herein incorporated by reference. The terms "guide RNA" and "gRNA" include both double-molecule gRNAs and single-molecule gRNAs. An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. The crRNA and the corresponding tracrRNA hybridize to form a gRNA. The crRNA additionally provides the single-stranded DNA-targeting segment that hybridizes to a CRISPR RNA recognition sequence. If used for modification within a cell, the exact sequence of a given crRNA or tracrRNA molecule can be designed to be specific to the species in which the RNA molecules will be used. See, for example, Mali et al. (2013) Science 339:823-826; Jinek et al. (2012) Science 337:816-821 ; Hwang et al. (2013) Nat. Biotechnol. 31 :227-229; Jiang et al. (2013) Nat. Biotechnol. 31 :233-239; and Cong et al. (2013) Science 339:819-823, each of which is herein incorporated by reference. The DNA-targeting segment (crRNA) of a given gRNA comprises a nucleotide sequence that is complementary to a sequence in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the Cas9 system and organism but often contain a targeting segment of between 21 to 72 nucleotides length, flanked by two direct repeats (DR) of a length of between 21 to 46 nucleotides (see, e.g., WO2014/131833). In the case of 5" pyogenes, the DRs are 36 nucleotides long and the targeting segment is 30 nucleotides long. The 3' located DR is complementary to and hybridizes with the corresponding tracrRNA, which in turn binds to the Cas9 protein.

The DNA-targeting segment can have a length of from about 12 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. Alternatively, the DNA-targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting segment that is complementary to a nucleotide sequence (CRISPR RNA recognition sequence) of the target DNA can have a length at least about 12 nt. For example, the DNA-targeting sequence (i.e., the sequence within the DNA-targeting segment that is complementary to a CRISPR RNA recognition sequence within the target DNA) can have a length at least about 12 nt, at least about 15 nt, at least about 18 nt, at least about 19 nt, at least about 20 nt, at least about 25 nt, at least about 30 nt, at least about 35 nt, or at least about 40 nt. Alternatively, the DNA-targeting sequence can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some cases, the DNA-targeting sequence can have a length of at about 20 nt.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild-type tracrRNA sequence (e.g., about or more than about 20, 26, 32, 45, 48, 54, 63, 67, 85, or more nucleotides of a wild-type tracrRNA sequence). Examples of wild-type tracrRNA sequences from S. pyogenes include 171 -nucleotide, 89-nucleotide, 75-nucleotide, and 65-nucleotide versions. See, for example, Deltcheva et al. (2011) Nature 471:602-607; WO 2014/093661, each of which is incorporated herein by reference in their entirety. Examples of tracrRNAs within single-guide RNAs (sgRNAs) include the tracrRNA segments found within +48, +54, +67, and +85 versions of sgRNAs, where "+n" indicates that up to the +n nucleotide of wild-type tracrRNA is included in the sgRNA. See U.S. Pat. No. 8,697,359, incorporated herein by reference in its entirety.

The percent complementarity between the DNA-targeting sequence and the CRISPR RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the CRISPR RNA recognition sequence within the target DNA can be at least 60% over about 20 contiguous nucleotides. As an example, the percent complementarity between the DNA-targeting sequence and the CRISPR RNA recognition sequence within the target DNA is 100% over the 14 contiguous nucleotides at the 5' end of the CRISPR RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the CRISPR RNA recognition sequence within the target DNA is 100% over the seven contiguous nucleotides at the 5' end of the CRISPR RNA recognition sequence within the complementary strand of the target DNA and as low as 0% over the remainder. In such a case, the DNA-targeting sequence can be considered to be 7 nucleotides in length.

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methy transferases, DNA demethylases, histone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the RNA. The DNA encoding the gRNA can encode a single RNA molecule (sgRNA) or separate RNA molecules (e.g., separate crRNA and tracrRNA). In the latter case, the DNA encoding the gRNA can be provided as separate DNA molecules encoding the crRNA and tracrRNA, respectively. DNAs encoding gRNAs can be stably integrated in the genome of the cell and operably linked to a promoter active in the cell. Alternatively, DNAs encoding gRNAs can be operably linked to a promoter in an expression construct.

Alternatively, gRNAs can be prepared by various other methods. For example, gRNAs can be prepared by in vitro transcription using, for example, T7 RNA polymerase (see, for example, WO 2014/089290 and WO 2014/065596). Guide RNAs can also be a synthetically produced molecule prepared by chemical synthesis.

(iii) C. CRISPR RNA Recognition Sequences

The term "CRISPR RNA recognition sequence" includes nucleic acid sequences present in a target DNA to which a DNA-targeting segment of a gRNA will bind, provided sufficient conditions for binding exist. For example, CRISPR RNA recognition sequences include sequences to which a guide RNA is designed to have complementarity, where hybridization between a CRISPR RNA recognition sequence and a DNA targeting sequence promotes the formation of a CRISPR complex. Full complementarity is not necessarily required, provided there is sufficient complementarity to cause hybridization and promote formation of a CRISPR complex. CRISPR RNA recognition sequences also include cleavage sites for Cas proteins, described in more detail below. A CRISPR RNA recognition sequence can comprise any polynucleotide, which can be located, for example, in the nucleus or cytoplasm of a cell or within an organelle of a cell.

The CRISPR RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001)). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a CRISPR RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "CRISPR RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends). Staggered ends can be produced, for example, by using two Cas proteins, each of which produces a single-strand break at a different cleavage site on each strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the CRISPR RNA recognition sequence of the nickase on the first strand is separated from the CRISPR RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas9 can occur at locations determined by both (i) base-pairing complementarity between the gRNA and the target DNA and (ii) a short motif, called the protospacer adjacent motif (PAM), in the target DNA. The PAM can flank the CRISPR RNA recognition sequence. Optionally, the CRISPR RNA recognition sequence can be flanked by the PAM. For example, the cleavage site of Cas9 can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-NiGG-3', where Ni is any DNA nucleotide and is immediately 3' of the CRISPR RNA recognition sequence of the non-complementary strand of the target DNA. As such, the PAM sequence of the complementary strand would be 5'-CC N2-3', where N2 is any DNA nucleotide and is immediately 5' of the CRISPR RNA recognition sequence of the complementary strand of the target DNA. In some such cases, Ni and N2 can be complementary and the Ni-N2 base pair can be any base pair (e.g., Ni=C and N2=G; Ni=G and N2=C; Ni=A and N2=T, Ni=T, and N2=A).

Examples of CRISPR RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas protein (see, for example, WO 2014/165825). The guanine at the 5' end can facilitate transcription by RNA polymerase in cells. Other examples of CRISPR RNA recognition sequences can include two guanine nucleotides at the 5' end (e.g., GGN2ONGG; SEQ ID NO: 9) to facilitate efficient transcription by T7 polymerase in vitro. See, for example, WO 2014/065596.

The CRISPR RNA recognition sequence can be any nucleic acid sequence endogenous or exogenous to a cell. The CRISPR RNA recognition sequence can be a sequence coding a gene product (e.g., a protein) or a non-coding sequence (e.g., a regulatory sequence) or can include both.

In one embodiment, the target sequence is immediately flanked by a Protospacer Adjacent Motif (PAM) sequence. In one embodiment, the gRNA comprises a third nucleic acid sequence encoding a Clustered Regularly Interspaced Short Palindromic Repeats (CRISPR) RNA (crRNA) and a trans-activating CRISPR RNA (tracrRNA). In another embodiment, the genome of the pluripotent cell comprises a target DNA region complementary to the target sequence. In some such methods, the Cas protein is Cas9. Active variants and fragments of nuclease agents (i.e. an engineered nuclease agent) may also be used. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strand-break-inducing activity. For example, any of the nuclease agents described herein can be modified from a native endonuclease sequence and designed to recognize and induce a nick or double-strand break at a recognition site that was not recognized by the native nuclease agent. Thus, in some embodiments, the engineered nuclease has a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site. The nuclease agent may be introduced into the cell by any means known in the art. The polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally or constitutive expressed within the cell. Thus, the polynucleotide encoding the nuclease agent can be contained in an expression cassette and be operably linked to a conditional promoter, an inducible promoter, a constitutive promoter, or a tissue-specific promoter. Alternatively, the nuclease agent is introduced into the cell as an mRNA encoding a nuclease agent.

In specific embodiments, the polynucleotide encoding the nuclease agent is stably integrated in the genome of the cell and operably linked to a promoter active in the cell. In other embodiments, the polynucleotide encoding the nuclease agent is in the same targeting vector comprising the insert polynucleotide, while in other instances the polynucleotide encoding the nuclease agent is in a vector or a plasmid that is separate from the targeting vector comprising the insert polynucleotide.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example the polynucleotide encoding the nuclease agent can be modified to substitute codons having a higher frequency of usage in a given eukaryotic cell of interest, as compared to the naturally occurring polynucleotide sequence.

Compositions

In certain aspects the present disclosure relates to a composition comprising isolated cells that have developed from a zygote, for example a zygote that has been generated or isolated in vitro. In some embodiments, the isolated cell line is an extraembryonic endodermal (XEN) cell line. In some embodiments, the isolated cell line is an embryonic fibroblast (EF) cell line. The in vitro zygote may be cultured for several days to generate the XEN cell line or the EF cell line. For example, in some embodiments, the zygote is cultured in vitro for at least 1, 2, 3, 4, 5, 6, 7, 8, 9, or 10 days to generate the XEN cell line or EF cell line. Any of these values may be used to define a range for the number of days that the zygote is cultured in vitro. For example, the zygote may be cultured for 1 to 10 days, for 4 to 6 days, or from 4 to 10 days.

In some embodiments, the isolated cell line is from a mammal, for example a human, a non-human mammal, a primate, a sheep, a goat, a cow, a pig or a horse. In a particular embodiment, the mammal is a sheep, a goat, a cow, or a pig.

The isolated XEN cell and the isolated EF cell may be identified by a particular expression profile of marker genes. For example, in some embodiments, the XEN cell line expresses one or more of GATA4, FOXA2, GATA6 and SOX17. In some embodiments, the XEN cell line does not express one or more of CDX2, NANOG, SOX2. In a particular embodiment, the XEN cell line expresses GATA4, FOXA2, GATA6 and SOX17, and does not express CDX2, NANOG, SOX2. In some embodiments the EF cell line expresses one or more of PDGFRa, uPA, Vimentin and GPC-1. In some embodiments, the EF cell line does not express one or more of NANOG, SOX2, CDX2, AFP, GATA4, GATA6, FOXA2, and SALL4. In a particular embodiment, the EF cell line expresses PDGFRa, uPA, Vimentin and GPC-1 and does not express NANOG, SOX2, CDX2, AFP, GATA4, GATA6, FOXA2, and SALL4.

The isolated XEN cell line and the isolated EF cell line may comprise a genetic modification. In some embodiments, the genetic modification is performed on the zygote cultured in vitro, and the XEN cell line and EF cell line develop from the genetically modified zygote. In other embodiments, the XEN cell line and EF cell line develop from a zygote cultured in vitro that is not genetically modified. For example, in some embodiments, the genetic modification is performed on the XEN cell line or the EF cell line. Methods of genetically modifying cells are known in the art and described herein.

The genetically modified XEN cell and the genetically modified EF cell may be used as the source of a nucleus for somatic cell nuclear transfer (SCNT). For example, in some embodiments the present disclosure provides an oocyte comprising a heterologous nucleus from a genetically modified XEN cell or a genetically modified EF cell described herein. For example, the nucleus of the oocyte may be removed and replaced with the nucleus from a genetically modified XEN cell or a genetically modified EF cell described herein. In some embodiments, the present disclosure relates to an embryo that develops from the oocyte comprising the heterologous nucleus. In some embodiments, the disclosure provides an embryo that comprises a nucleus isolated from a genetically modified XEN cell or a genetically modified EF cell described herein. The XEN cell or EF cell may be isolated from the developing embryo and stored for further use.

Methods

The present disclosure also relates to a method of mutagenizing an XEN cell or an EF cell or pluralities of either or both of the same comprising contacting the XEN cell and/or the EF cell with one or more components of a CRISPR system, such CRISPR system comprising a nucleic acid sequence comprising an sgRNA comprising at least one or a combination of domains from a 5' to 3' orientation: a DNA-binding domain, a Cas-protein binding domain, and a transcription terminator domain, wherein each domain comprises from about 1 to about 150 nucleotides. In some embodiments, the entire sgRNA comprises no more than about 110, 105, 104, 103, 102, 101, 100, 99, 98, 97, 96 or 95 or fewer nucleotides. In some embodiments, any of the methods comprise the step of contacting a biophysically effective amount of one or a plurality of CRISPR system components to the XEN cell and/or EF cell for a period of time sufficient to modify the genome of the XEN cell and/or EF cell.

In some embodiments, the present disclosure relates to a method of creating a transgenic mammal (such as, for example, a mammal that is a pig, goat, sheep, cow or horse), the method comprising:

(a) obtaining one or a plurality of XEN cells;

(b) mutagenizing the one or plurality of XEN cells by exposing the cell to a biophysically effective amount of a gene-modifying amino acid sequence and/or gene-modifying nucleic acid until at least one of the XEN cells becomes mutagenized;

(c) identifying the one or plurality of mutagenized XEN cells;

(d) transplanting or injecting nuclei from the one or plurality of mutagenized cells into an oocyte such that the oocyte has the genetic information necessary to becomes an embryo comprising mutagenized cells;

(e) implanting the embryo comprising mutagenized cells into a female host, and, optionally, allowing the embryo to grow into a fetus. In some embodiments, the step of obtaining one or a plurality of XEN cells comprises isolating a cell with an endodermal lineage or morphology from a blastocyst and culturing those isolated endodermal cells in cell culture medium for about 1, 2, 3, 4, 5, or more days. In some embodiments, the blastocyst is in culture from about 3 to about 5 days before isolation of the endodermal cells is performed.

In some embodiments, the present disclosure relates to a method of creating a transgenic mammal (such as, for example, a mammal that is a pig, goat, sheep, cow or horse), the method comprising:

(a) obtaining one or a plurality of EF cells;

(b) mutagenizing the one or plurality of EF cells by exposing the cell to a biophysically effective amount of a gene-modifying amino acid sequence and/or gene-modifying nucleic acid until at least one of the EF cells becomes mutagenized and/or comprises a genetic modification;

(c) identifying the one or plurality of mutagenized EF cells;

(d) transplanting or injecting nuclei from the one or plurality of mutagenized cells into an oocyte such that the oocyte has genetic information necessary to becomes an embryo comprising mutagenized cells;

(e) implanting the embryo comprising mutagenized cells into a female host, and, optionally, allowing the embryo to grow into a fetus. In some embodiments, the step of obtaining one or a plurality of EF cells comprises isolating a cell with a mesodermal lineage or morphology from a blastocyst and culturing those isolated mesodermal cells in cell culture medium for about 1, 2, 3, 4, 5, or more days. In some embodiments, the blastocyst is in culture from about 3 to about 5 days before isolation of the mesodermal cells is performed.

In some embodiments, any of the methods disclosed herein comprise a step of identifying wherein the step comprise contacting the one or plurality of mutagenized XEN cells or EF cells with a probe specific for the genetic modification.

The present disclosure relates to a method of forming or culturing a composition comprising endodermal cell or mesodermal cells in vitro, the method comprising:

(a) culturing a zygote for a time period sufficient to create a blastocyst;

(b) isolating an endodermal cell and/or mesodermal cells from the blastocyst in cell culture medium and allowing a sufficient period of time to propagate the endodermal and/or mesodermal cells in the culture medium. In some embodiments, the endodermal cell comprises or consists of a XEN cell line. In other embodiments, the mesodermal cells comprise or consist of an EF cell line. In some embodiments, the blastocyst is not derived from fetal cells or fetal tissue.

The present disclosure also relates to to method of making or culturing a composition of comprising endodermal cell or mesodermal cells in vitro, the method comprising: exposing one or a plurality of XEN cells and/or one or a plurality of EF cells to any tissue culture medium disclosed in the disclosure, including the Examples. In some embodiments the methods in which the nuclei of XEN cells or EF cells of one species are transferred to a oocyte from the same species, the method comprise selecting or screening for one or a plurality of XEN cells or EF cells comprising a genetic modification.

The present disclosure also relates to a method of producing a germline mutation in a mammal, the method comprising (a) contacting a biophysically effective amount of a gene-modifying amino acid sequence and/or gene-modifying nucleic acid sequence with one or a plurality of XEN cells and/or or EF cells such that one or a plurality of Xen cells and/or EF cells comprise a knock-in, knockout, deletion or point mutation; and (b) screening the one or plurality of XEN cells and/or the one or plurality of EF cells for a genetic modification (such as a knock-in, knock-out, point mutation or deletion); and, optionally, culturing blastocysts from a zygote of a mammal on feeder cells in culture medium for a time period sufficient to produce one or a plurality of XEN cells and/or one or a plurality of primary EF cells before step (a). In some embodiments, the method further comprises isolating one or more nuclei from the one or plurality of XEN cells and/or EF cells and injecting the one or more nuclei into an oocyte of a mammal after the step of screening.

(i) culturing the oocyte for a time period sufficient to produce a mammalian embryo; and (ii) implanting the mammalian embryo into a host mammal to produce a genetically modified mammal comprising the genetic modification.

The disclosure also relates to a method of detecting the presence or absence of a genetic modification in a cell based upon measurements of the probes specific for the genetic modification of interest. The method may comprise a step of quantifying the amount of RNA or protein expression on a cell or plurality of cells by exposing cells known to comprise or suspected of comprising the genetic modification to one or a plurality of probes known to associate, bind or enzymatically alter the expression products above. The data collected on the number and concentration of expression products, can be used as evidence to correlate the signature or detection of the presence of endodermal cells or mesodermal cells like XEN cells or EF cells in a cell culture device.

The disclosure relates to any disclosed method in which the animal is generated with crossing or breeding an F1 or F2 generation of animals.

In some aspects of the disclosure, the methods disclosed herein comprise a step of culturing the embryo in vitro before transfer into a recipient female mammal and laparoscopic or non-surgical transfer may be practiced in many variations. Variations are described more fully in PCT/US2005/034641, which is herein incorporated by reference in its entirety. In certain embodiments, the embryo may be from any mammal and in some embodiments is porcine, equine, bovine, caprine or oovine. In various embodiments, the embryo may be produced by in nuclear injection of material from XEN cells or EF cells into oocytes from mammals, in vitro fertilization or by cloning. In certain embodiments, the embryo may be transgenic or non-transgenic. In some embodiments, the embryo is transferred when it is at least at the 2-cell stage, at least at the 4-cell stage, at least at the 8-cell stage, at least at the 16-cell stage, at least at the morula stage, at least at the blastocyst stage, at least at the expanding blastocyst stage, at least at the hatching blastocyst stage, or at least at the blastula stage. In other embodiments, the embryo is transferred when it has been cultured in vitro for at least about 18 hours, at least about 24 hours, at least about 48 hours, at least about 72 hours, at least about 76 hours, at least about 80 hours, at least about 84 hours, at least about 90 hours, at least about 96 hours, at least about 102 hours, at least about 108 hours, at least about 114 hours, at least about five days, at least about five and one-half days, at least about six days, at least six and one-half days, at least seven days, at least seven and one-half days, at least eight days, at least eight and one-half days, or at least nine days after injection of nuclear material from the XEN cells or EF cells. In a preferred embodiment, the embryos are cultured in a media such as PZM or NCSU at a temperature range of 36° C. to 40° C. under humid atmosphere containing 3.5% to 6.5% $CO_2$ with any appropriate range of $O_2$, more preferably 38.5° C. in 5% $CO_2$:5% $O_2$. In another embodiment, the embryo may be stored in any atmosphere where the media is under oil to prevent evaporation.

In various embodiments, the transfer can be accomplished by surgical or non-surgical methods or by minimally invasive methods, i.e., laparoscopic methods. In preferred embodiments, the site of transfer is the uterus, most preferably, the tip, middle or base of the uterine horn, or in the uterus body itself.

In various embodiments, the efficiency of transfer and live birth is at least one and one-half times, at least two times, at least three times, at least four times, or at least five times more efficient than existing techniques. Alternatively the efficiency of transfer and live birth may be expressed as at least about 4, 5, 6, 7, 8, 9, 10, 11, 12 or more percent live births per transfer for the method claimed. Alternatively, the efficiency of transfer and live birth may be expressed in terms of the recipient farrowing rate (i.e., the % of recipients that become pregnant and go to term) and/or the average litter size per farrowing recipient. In preferred embodiments, the recipient farrowing rate is at least about 30%, at least about 40%, at least about 50%, at least about 60%, at least about 70% or at least about 80%. The average litter size for each farrowing recipient is at least 4 piglets, at least 5 piglets or at least 6 piglets. In various embodiments, the recipient animal may be a gilt (young virgin female) or, more preferably, a sow in its peak reproductive age or, even more preferably, a sow of proven maternal abilities In certain aspects, the present disclosure involves genetic modification of XEN cells or EF cells to inactivate a gene or a plurality of genes by multiplex genomic editing using the CRISPR/Cas9 system described herein. Thus, embodiment include targeting 1, 2, 3, 4, 5 or more targets in a multiplex approach. Some traits, like cancer, are caused on the basis of mutations at multiple genes (see APC/p53). In addition numerous disease traits are so-called Complex traits that manifest as a result of the influence of alleles at more than one gene. For example, diabetes, metabolism, heart disease, and neurological diseases are considered complex traits. Thus, embodiments include animals that are heterozygous and homozygous for individual alleles, or in combination with alleles at other genes, in different combinations. For example mature onset diabetes of the young (MODY) loci cause diabetes individually and additively, including; MODY 1 (HNF4a), MODY 2 (GCK), MODY 3 (HNF1a), MODY 4 (Pdx1), MODY 5 (HNF-Iβ), MODY 6 (eurogenic differentiation 1), MODY 7 (KLF11), MODY 8 (CEL), MODY 9 (PAX4), MODY 10 (INS), MODY 11 (BLK). Livestock cells, such as XEN cells and/or EF cells or embryos derived from the nuclear transfer of the same can be subjected to multiplex editing of numerous genes for animal modelling, including various disease modeling targets: APC, ApoE, DMD, GHRHR, HR, HSD11B2, LDLR, NF1, NPPA, NR3C2, p53, PKD1, Rbm20, SCNN1G, tP53, DAZL, FAH, HBB, IL2RG, PDX1, PITX3, Runx1, RAG2, GGTA.

The disclosure relates to a method of increasing the efficiency of farrowing or generation of a genetically modified animal, the method comprising implanting an embryo derived from a XEN cell or an EF cell. In some embodiments, the method comprises:

(a) obtaining one or a plurality of XEN cells and/or one or a plurality of EF cells;

(b) mutagenizing the one or a plurality of XEN cells and/or one or a plurality of EF cells by exposing the cells to a biophysically effective amount of a gene-modifying amino acid sequence and/or gene-modifying nucleic acid until at least one of the XEN cells becomes mutagenized;

(c) identifying the one or plurality of mutagenized XEN cells and/or one or a plurality of mutagenized EF cells;

(d) transplanting or injecting nuclei from the one or plurality of mutagenized cells into an oocyte such that the oocyte has the genetic information necessary to becomes an embryo comprising mutagenized cells;

(e) implanting the embryo comprising mutagenized cells into a female host, and, optionally, allowing the embryo to grow into a fetus.

The genetically modified animals of the present disclosure and progeny thereof as well as genetically modified XEN cells or EF cells are useful in studying the mechanisms behind gene function such as by loss-of-function genetic modifications as well as creating disease models. Additionally, the animals can be used to test compounds useful in treating and diagnosing human diseases. Accordingly, methods of screening assays are provided herein for identifying modulators, i.e., candidate or test compounds or agents (e.g., peptides, cyclic peptides, peptidomimetics, small molecules, small organic molecules, or other drugs) which effect (i.e., modulate, inhibit, reduce, prevent or reverse) diseases.

For example, the genetically modified animals provided herein can be used as models for cancer, autoimmune diseases or genetic disorders. In some embodiments, the disorder is a monogenic disorder. In some embodiments, the disorder is a multigenic disorder. In some embodiments, the disorder is a disorder associated with one or more single nucleotide polymorphisms (SNPs). Exemplary disorders associated with one or more SNPs include a complex disease described in U.S. Pat. No. 7,627,436, Alzheimer's disease as described in PCT International Application Publication No. WO/2009/112882, inflammatory diseases as described in U.S. Patent Application Publication No. 2011/0039918, polycystic ovary syndrome as described in U.S. Patent Application Publication No. 2012/0309642, cardiovascular disease as described in U.S. Pat. No. 7,732,139, Huntington's disease as described in U.S. Patent Application Publication No. 2012/0136039, thromboembolic disease as described in European Patent Application Publication No. EP2535424, neurovascular diseases as described in PCT International Application Publication No. WO/2012/001613, psychosis as described in U.S. Patent Application Publication No. 2010/0292211, multiple sclerosis as described in U.S. Patent Application Publication No. 2011/0319288, schizophrenia, schizoaffective disorder, and bipolar disorder as described in PCT International Application Publication No. WO/2006/023719A2, bipolar disorder and other ailments as described in U.S. Patent Application Publication No. U.S. 2011/0104674, colorectal cancer as described in PCT International Application Publication No. WO/2006/104370A1, a disorder associated with a SNP adjacent to the AKT1 gene locus as described in U.S. Patent Application Publication No. U.S. 2006/0204969, an eating disorder as described in PCT International Application Publication No. WO/2003/012143 A1, autoimmune disease as described in U.S. Patent Application Publication No. U.S. 2007/0269827, fibrostenosing disease in patients with Crohn's disease as described in U.S. Pat. No. 7,790,370, and Parkinson's disease as described in U.S. Pat. No. 8,187,811, each of which is incorporated herein by reference in its entirety.

Animals of any species, including, but not limited to rabbits, guinea pigs, pigs, mini-pigs, goats, cows, sheep or horses, and may be used to generate disease animal models. These systems may be used in a variety of applications. Such assays may be utilized as part of screening strategies designed to identify agents, such as compounds that are capable of ameliorating disease symptoms. Thus, the animal- and cell-based models may be used to identify drugs, pharmaceuticals, therapies and interventions that may be effective in treating disease.

EXAMPLES

Example 1. Derivation of Primary Cell Lines from Pig Embryos

Figure 2:
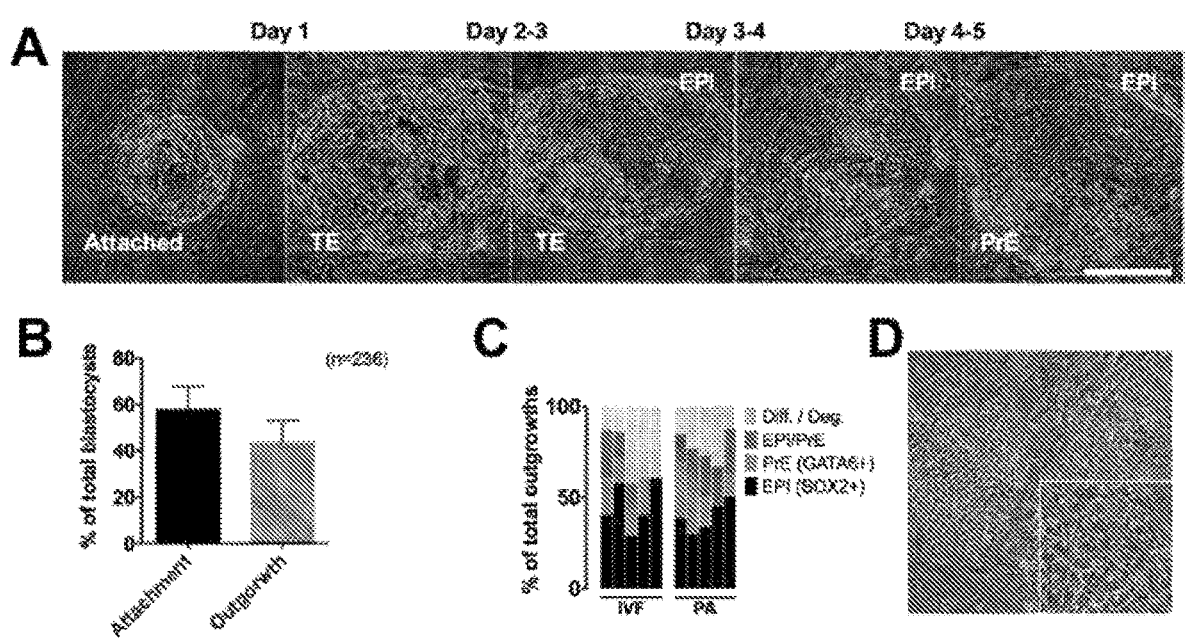
FIG. 2 shows primary outgrowths from Day 7 pig blastocysts. (A) Representative micrographs of porcine blastocysts attached to the feeders and establishing primary outgrowths. In the panels, TE stands for trophectoderm; EPI is epiblast; and PrE is primitive endoderm. (B) Percentage of the blastocyst with attachment and outgrowth (5 replicated, n=236). (C) The percentage of cell sub-populations in primary colonies were calculated by its morphology with specific lineage marker (SOX2$^+$/GATA6$^+$) expression. (D) Morphology of extraembryonic endoderm cells; cuboidal epithelial cells that tightly packed with one or two large lipid droplets. Scale bar: 100 μm.

We investigated the rate of attachment and primary outgrowth development from pig blastocyst (Day 7) explants. After treatment of blastocysts with acid tyrode, zona-free blastocysts were seeded onto mitotically inactivated (Mitomycin C treated) CF1 mouse embryonic fibroblasts (MEFs) in culture medium, containing high-glucose Dulbecco's modified Eagle medium (DMEM, Gibco), 20% ES-qualified fetal calf serum, 0.145 mg/ml L-glutamine, 100 units/ml penicillin-streptomycin, 0.5% NEAA, 5 ng/ml human LIF and 10 ng/ml bFGF. The cells were cultured in humidified conditions with 5% $O_2$, 5% $CO_2$ and 90% $N_2$ at 38.5° C. Following attachment, initial embryo outgrowth became flattened and spread slowly out [FIG. 2A]. The rates of blastocyst attachment and outgrowth were 57.9% and 43.6%, respectively [FIGS. 2B and C]. After 5 days, three early distinct lineages (epiblast, trophoblast, and primitive endoderm cells) can be seen in the initial outgrowth, which can be readily distinguished by morphological features and expression of known lineage-specific markers. At 8 days in culture, epiblast and primitive endoderm cells proliferated continuously, while trophoblast cells mostly faded. Epiblast cells underwent a change in morphology toward a fibroblast cell-like appearance and primitive endoderm-derived cells grew continuously and propagated as a single layer of loosely grouped cells [FIG. 2D]. The outgrowths and primary growths were mechanically dissociated into small clumps, and transferred onto fresh feeders for passaging. The media were changed every two days, and cells were passaged every 7-9 days. The two types of primary embryonic cell lines from Day 7 pig blastocysts could be routinely established in culture from a range of embryos including unfertilized parthenotes, as well as in vitro and in vivo fertilized embryos [Table 1]. XEN cells enabled a clear distinction from the EPI or differentiated cells with their morphology, allowing for easy dissociation of these cells.

Figure 3:
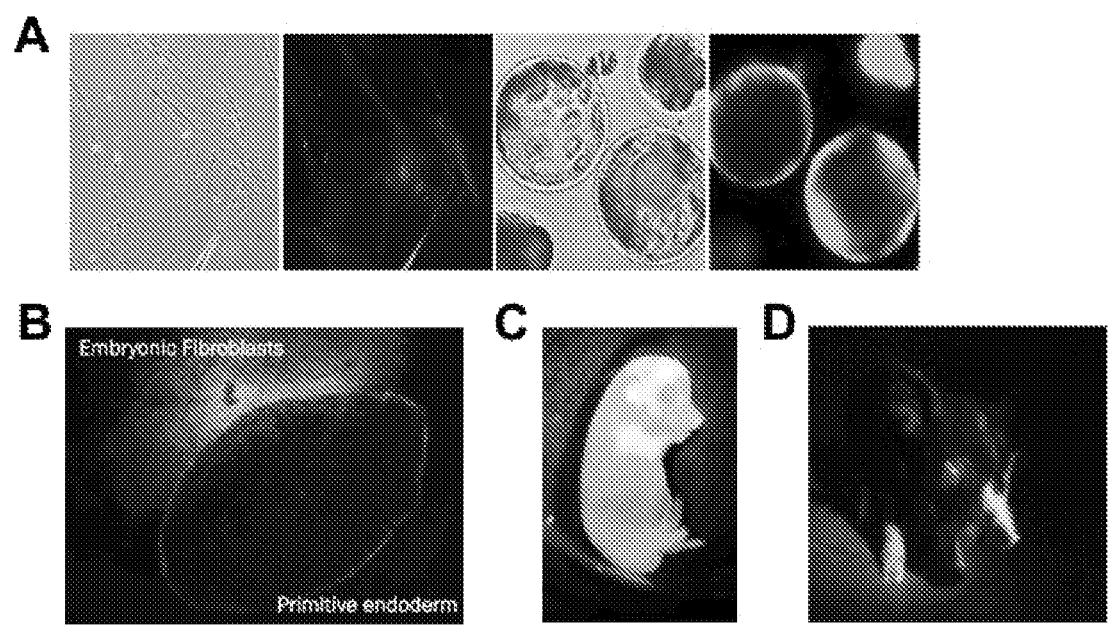
FIG. 3 shows generation of Embryonic fibroblasts and XEN cell derived fetuses and live piglets. (A) Representative light and fluorescent micrographs of primary porcine fetal fibroblasts transgenic for GFP and cloned embryos expressing GFP. (B) Primary explants showing embryonic fibroblasts and primitive endoderm cells. (C) Representative cloned fetus from embryonic fibroblasts obtained from day 39 of pregnancy. (D) live GFP cloned offspring generated using XEN cells as donors.
Figure 4A:
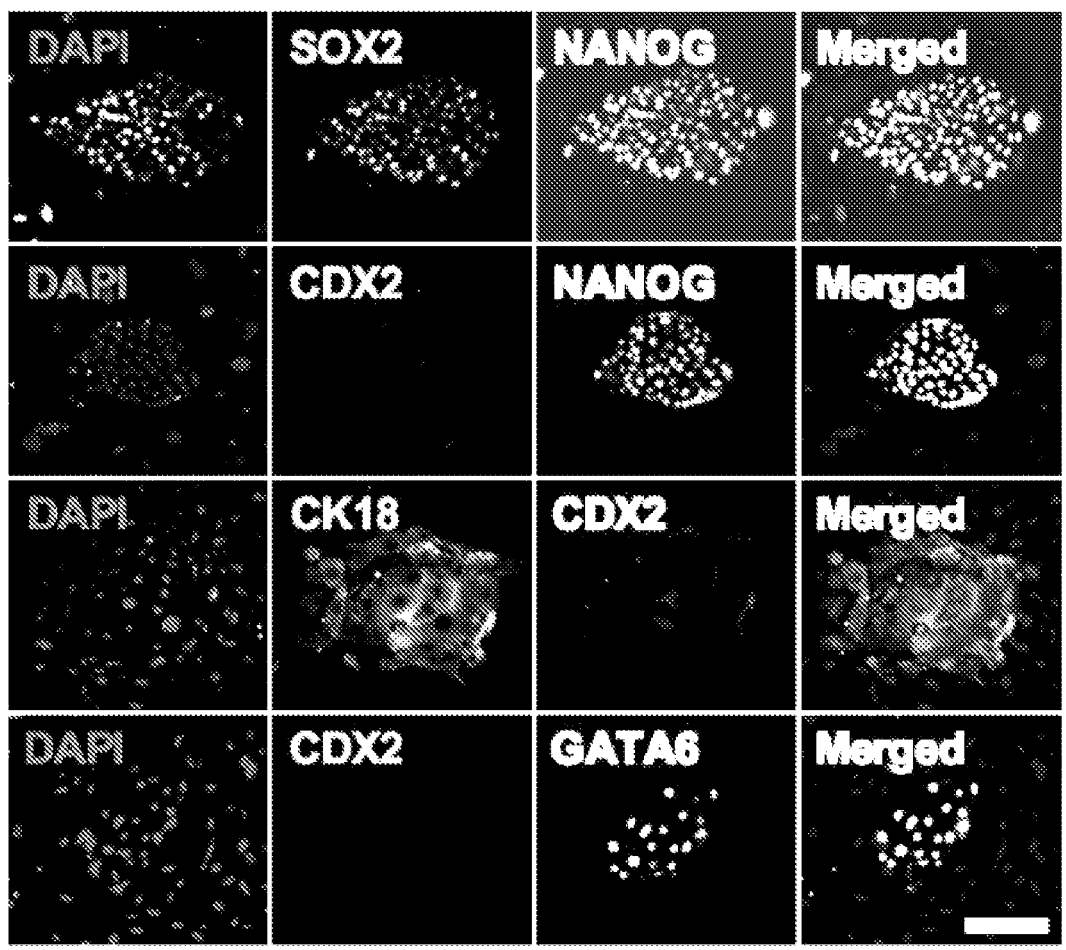
FIG. 4 shows lineage specific marker expression in primary colonies. Three early distinct lineages (EPI, TE, and PrE cells) are seen in the initial outgrowth at different time points during culture, which can be readily distinguished by morphological features and expression of known lineage-specific markers.
Figure 4B:
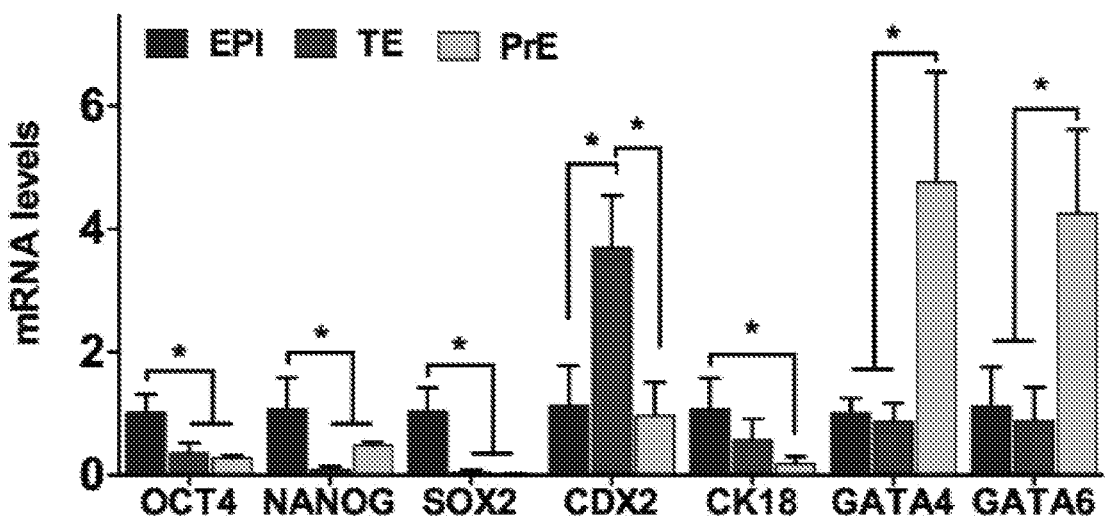
Figure 5:
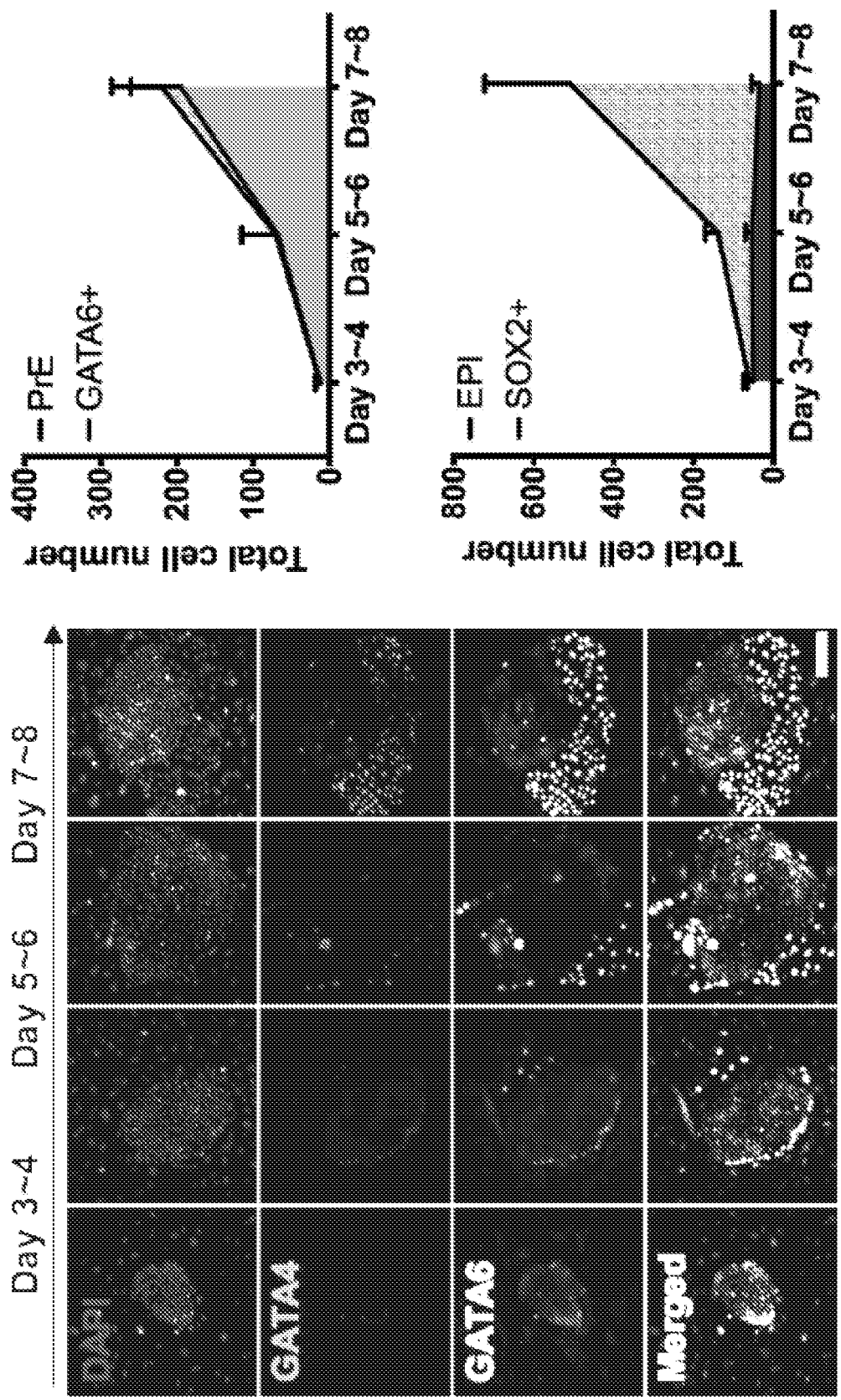
FIG. 5 shows proliferation and marker expression in PrE cells and EPI cells.
Figure 6:
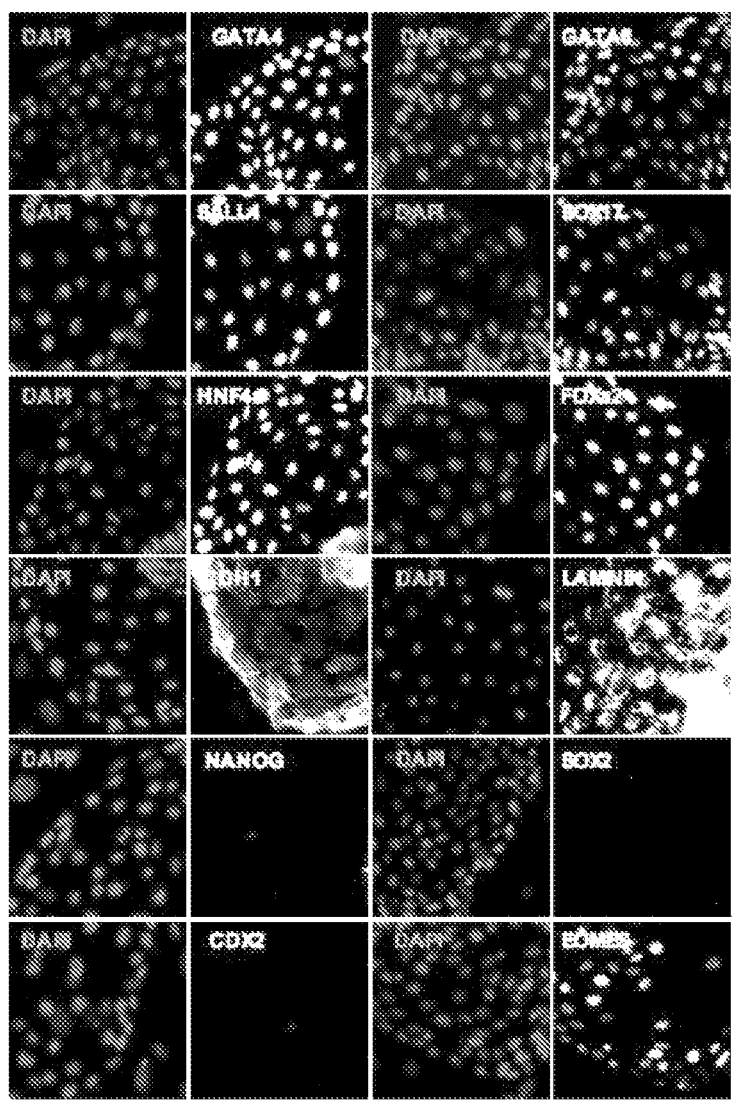
FIG. 6 shows the characterization of a derived XEN cell line. Quantitative PCR (qPCR) and immunocytochemical (ICC) analyses showed that these cells express high levels of endodermal lineage markers (GATA4, GATA6, FOXA2 and SOX17) and SALL4, which is known to contribute to the regulation of stemness of XEN cells that is comparable with previous reports. The other lineage markers (SOX2, NANOG, CDX2, HAND1) were negatively stained, but, interestingly, EOMES, which is a TE marker, was strongly expressed in these cells which is similar to rat XEN cells.
Figure 6:
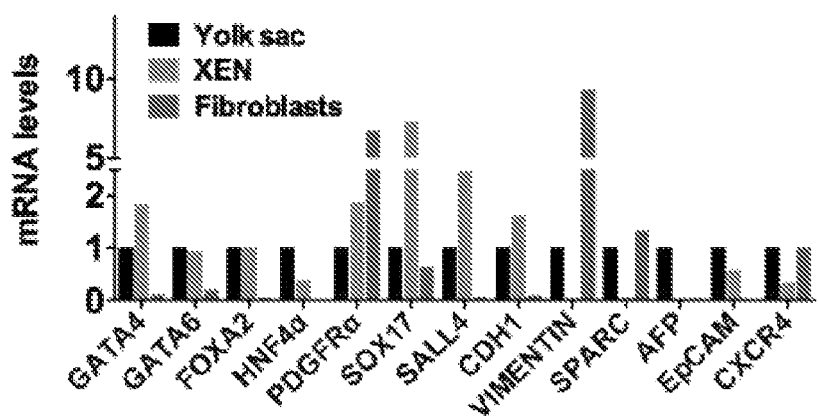
Figure 7:
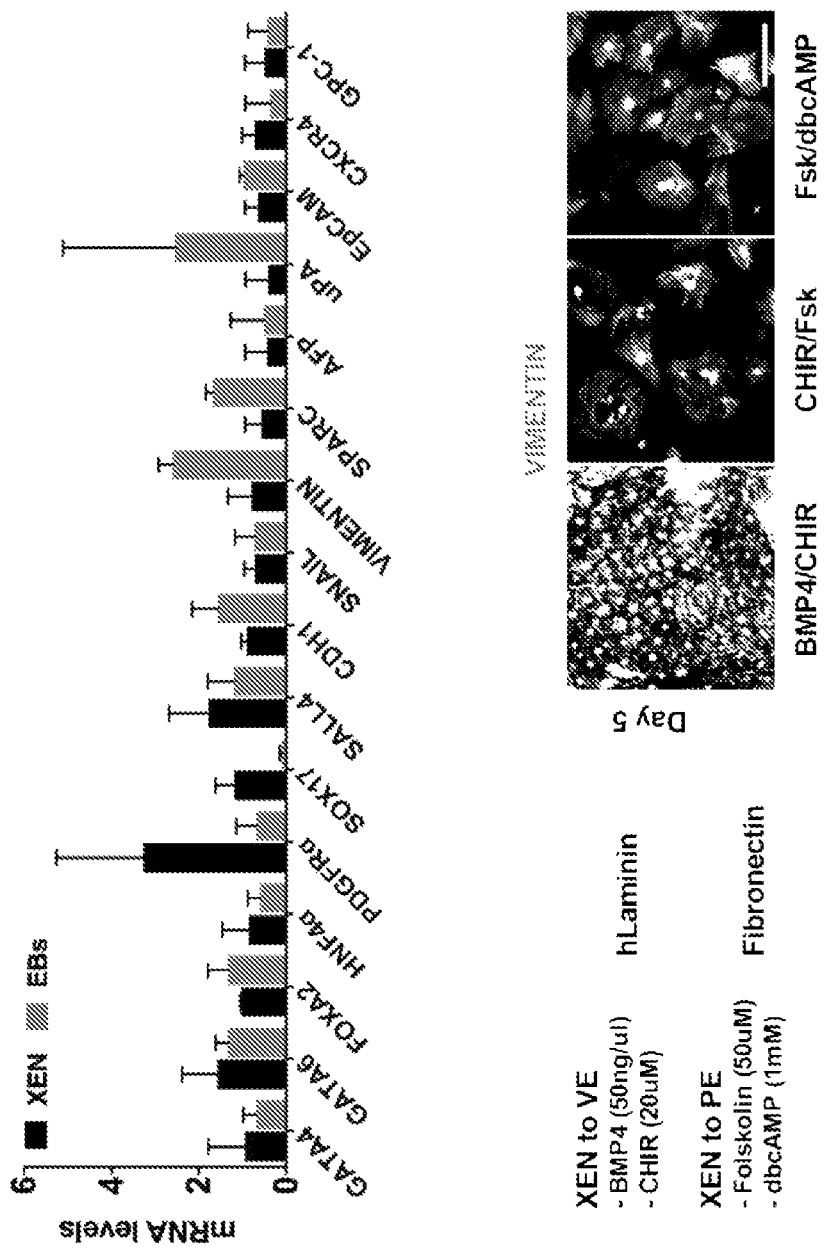
FIG. 7 shows spontaneous and directed differentiation of XEN cell lines. XEN cells were subjected to the embryoid body (EB) formation assay using a hanging drop method. XEN cells were differentiated into the more differentiated visceral and parietal XEN stages, visceral endoderm (VE) or parietal endoderm (PE) using treatment either with BMP4 ligands/CHIR99021 to activate Wnt or with dibutyric cAMP/forskolin for the elevation of cAMP pathway. As depicted in FIG. 7, stimulating Wnt signaling, led to a change of its morphology and increase of VE specific gene expression.
Figure 8:
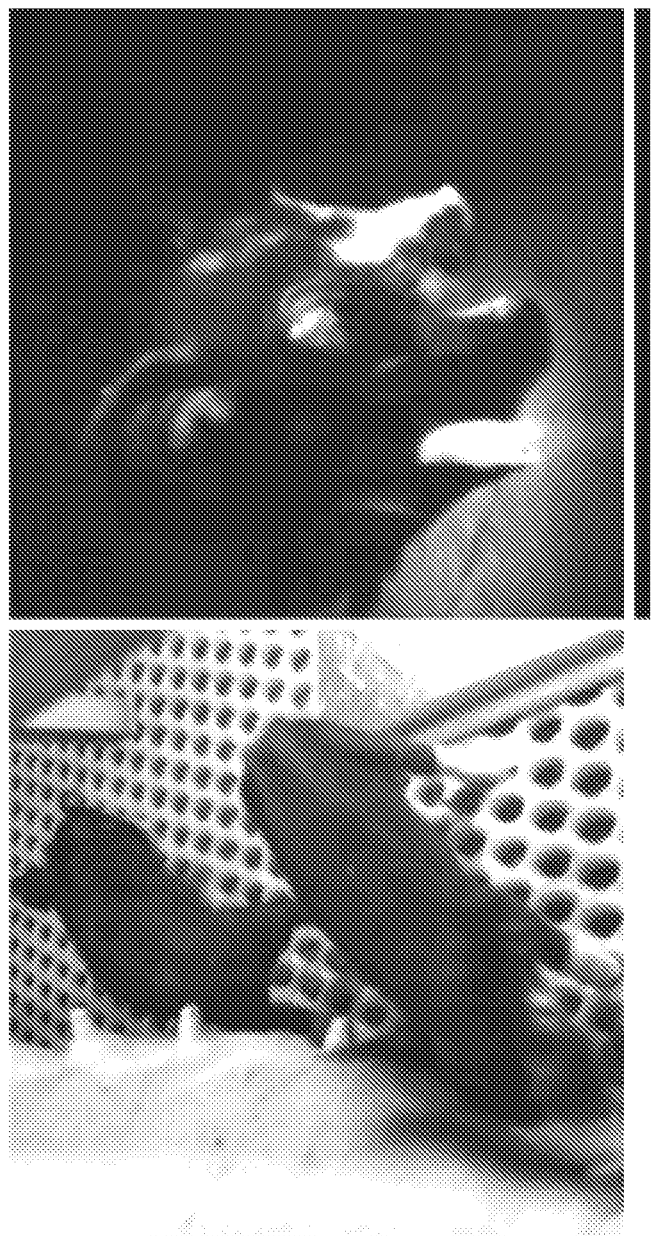
FIG. 8 shows live animals generated using XEN GFP-Col-KI cells as a nuclear donor.
Figure 9:
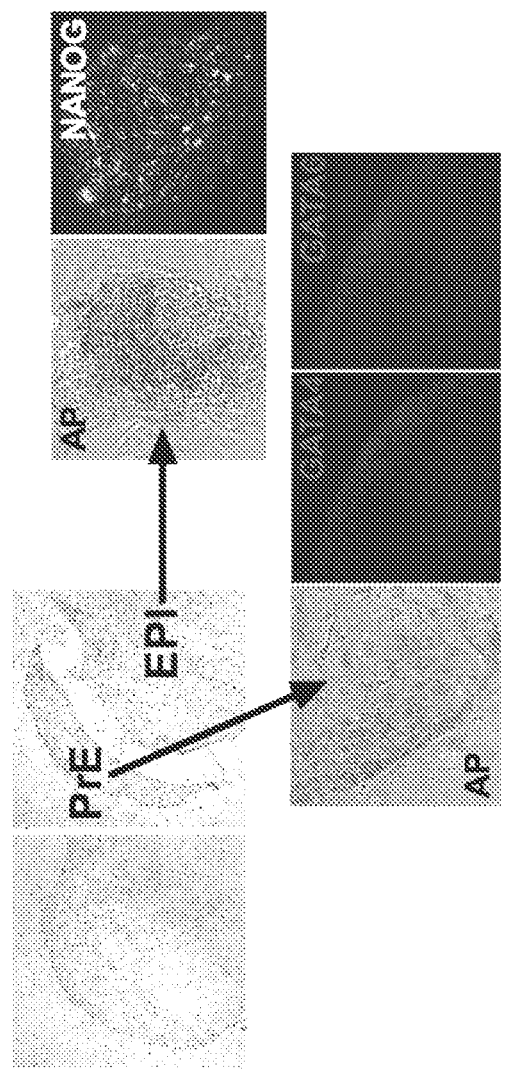
FIG. 9 shows light and fluorescent micrographs showing methodologies for establishment of Primitive endoderm derived XEN cells and Epiblast (EPI) derived embryonic fibroblasts. In the section, the EPI cells are identified by alkaline phosphatase (AP) staining, and expression of pluripotency marker (NANOG) (top right), and AP staining and expression of endodermal markers, GATA4 and GATA6 (bottom).
Figure 10:
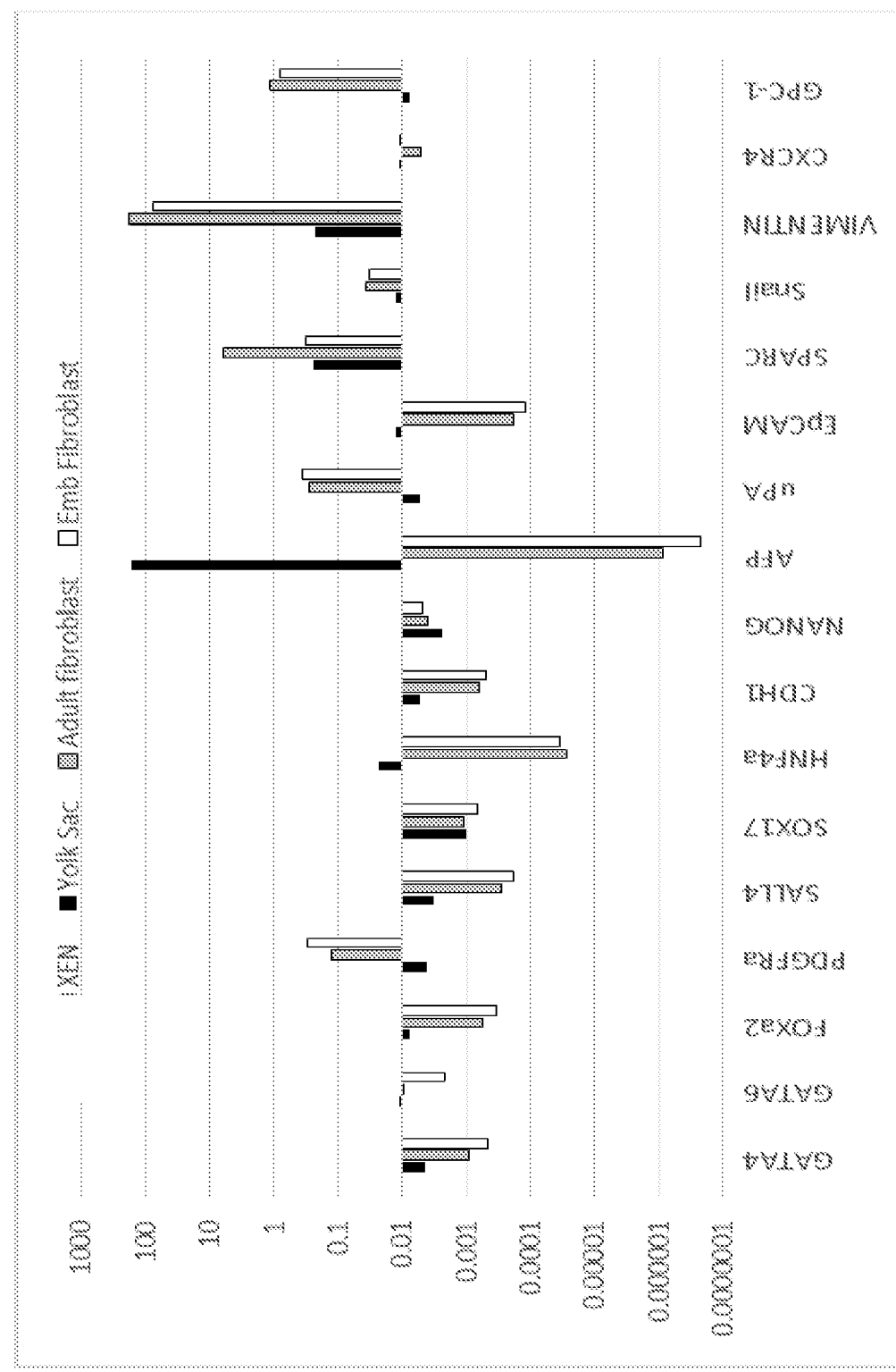
FIG. 10 shows Real time RT PCR data showing relative expression of candidate endodermal (GATA4; GATA6; FOXA2; SOX17), pluripotent genes (SALL4; NANOG;), committed endodermal genes (AFP, HNF4a), Cadherin, and other candidate fibroblast progenitor cells genes (PDGFRa; uPA, SPARC, Snail, VIMENTIN; GPC-1), of embryonic yolk sac, adult fetal fibroblast and embryo fibroblast as a fraction of expression in XEN cells.

Example 2. Nuclear Transfer using the Embryonic Cells for Generation of Gene-Edited Pigs To test the ability of established primary embryonic fibroblasts (EFs) as nuclear donors, we have utilized fetal fibroblasts expressing a constitutively expressed GFP knocked-in downstream of the COL1A sequence [FIG. 3A] and generated cloned zygotes. The GFP construct including a hUBC promoter, GFP coding region, and 5' and 3' targeting arms is provided as SEQ ID NO: 1. The Col1A sgRNA spacer sequence is provided as SEQ ID NO: 2. The embryos were cultured to blastocyst and the two primary cell lineages from epiblast and primitive endoderm cells that result in EF and XEN cells were established in culture as above [Table 1]. A representative EF and XEN line with a strong and consistent expression of GFP were used as nuclear donor for somatic cell nuclear transfer (SCNT) [FIG. 3B]. SCNT was performed as described in a previous study (Park, K. E. et al., 2016, International journal of molecular sciences 17). Briefly, cumulus-oocyte complexes (COCs) were purchased from a commercial supplier (De Soto Biosciences). The matured oocytes were enucleated by aspirating the polar body and MII chromosomes with an enucleation pipette (Humagen, Charlottesville, Va.). Embryo-derived cells were dissociated into single cells with accutase at 37° C. for 5 min followed by gentle pipetting. After enucleation, a donor cell was introduced into the perivitelline space of an enucleated oocyte. Fusion of injected oocytes was induced by DC pulse (2.0 kV/cm for 30 μs using a BTX-Cell Manipulator 2001 (BTX)). After fusion, the reconstituted oocytes were activated by an electric pulse (1.0 kV/cm for 60 μs), followed by 4 h of incubation in PZM3 medium containing 2 mM 6-dimethylaminopurine (6-DMAP). SCNT embryos were in vitro cultured for 24 hr and embryos at the 1-2 cell stage were surgically transferred into the oviducts of synchronized gilts on the first day of standing estrus. A total of 50 (EF) and 45 (XEN) reconstituted embryos were transferred into a surrogate gilt. Pregnancies were confirmed by ultrasound on day 30 following transfer. Five fetuses derived from EF were harvested from pregnant day 39 euthanized sow (FIG. 3C), whereas three piglets from XEN cells [Table 2] were allowed to progress to term and deliver live offspring at 115 day. Accordingly, these experiments have demonstrated that both EF and XEN cells are efficient sources for SCNT/ cloning and derivation of fetuses. GFP localization was examined using the epifluorescent microscope.

Summary: These results demonstrate for the first time the successful establishment of EF and XEN cells and their subsequent use as nuclear donors to generate live offspring for agricultural and biomedical applications.

TABLE 1

Establishment of embryo derived cells, primitive endoderm and embryonic fibroblast like cells from primary embryos. "PG" stands for parthenote derived embryos, "Vivo" stands for IVF derived ex vivo derived embryos; "SCNT" stands for somatic cell nuclear transfer/cloning derived embryos; "COL1-GFP" stands for stable GFP transgene knocked in downstream of COL1A locus.

| Cell line | Origin | Cell type | Passage No. |
|---|---|---|---|
| PG-1 | Parthenote | Primitive endoderm | 20 |
| PG-2 | Parthenote | Primitive endoderm | 6 |
| PG-2 | Parthenote | Fibroblast-like | 3 |
| PG-3 | Parthenote | Primitive endoderm | 5 |
| PG-2 | Parthenote | Fibroblast-like | 3 |
| PG-4 | Parthenote | Primitive endoderm | 3 |
| PG-5 | Parthenote | Primitive endoderm | 3 |
| PG-6 | Parthenote | Primitive endoderm | 3 |
| PG-7 | Parthenote | Primitive endoderm | 3 |
| PG-8 | Parthenote | Primitive endoderm | 3 |
| PG-9 | Parthenote | Primitive endoderm | 3 |
| PG-10 | Parthenote | Primitive endoderm | 3 |
| PG-11 | Parthenote | Primitive endoderm | 3 |
| Vivo-2 | Ex vivo | Primitive endoderm | 7 |
| Vivo-9 | Ex vivo | Primitive endoderm | 19 |
| Col1- GFP#3-1 | SCNT | Primitive endoderm | 10 |
| Col1- GFP#3-1 | SCNT | Fibroblast-like | 5 |
| Col1- GFP#3-2 | SCNT | Primitive endoderm | 10 |
| Col1- GFP#3-3 | SCNT | Fibroblast-like | 2 |
| Col1- GFP#33 | SCNT | Primitive endoderm | 10 |

TABLE 2

Efficiency of generating pigs using different types of donor cells for SCNT. FF stands for fibroblasts derived from fetus; EF stands for embryonic fibroblasts and XEN refers to Extra-embryonic endoderm cells. Cloning efficiency refers to a fraction of fetuses established/number of embryos transferred.

| Cell type | No. transferred | No. pregnancy | No. developed | No. fetuses (piglets) | Cloning Efficiency* |
|---|---|---|---|---|---|
| Fetal fibroblast (FF)- control | 104 | 1/1 | 1/1 (D115) | 5 | 4.9 |

TABLE 2-continued

Efficiency of generating pigs using different types of donor cells for SCNT. FF stands for fibroblasts derived from fetus; EF stands for embryonic fibroblasts and XEN refers to Extra-embryonic endoderm cells. Cloning efficiency refers to a fraction of fetuses established/number of embryos transferred.

| Cell type | No. transferred | No. pregnancy | No. developed | No. fetuses (piglets) | Cloning Efficiency* |
|---|---|---|---|---|---|
| GFP-KI Embryonic fibroblast (EF) | 50 | 1/1 | 1/1 (D39) | 6 | 12.0 |
| GFP-KI Primitive endoderm (XEN) | 45 | 1/1 | 1/1 (D115) | 3 | 6.7 |

*Cloning efficiency that was obtained by total no. fetus/total no. transferred embryos

TABLE Y

CRISPR enzymes (Cas proteins or Cas-like proteins) organized by Family

| Proposed gene name‡ | System type or subtype | Name from Haft et al.§ | Name from Brouns et al.§ | Structure of encoded protein (PDB accessions)¶ | Families (and superfamily) of encoded protein#** | Representatives |
|---|---|---|---|---|---|---|
| cas1 | Type I Type II Type III | cas1 | cas1 | 3GOD, 3LFX and 2YZS | COG1518 | SERP2463, SPy1047 and ygbT |
| cas2 | Type I Type II Type III | cas2 | cas1 | 2IVY, 2I8E and 3EXC | COG1343 and COG3512 | SERP2462, SPy1048, SPy1723 (N-terminal domain) and ygbF |
| cas3' | Type I‡‡ | cas3 | cas3 | NA | 1203 | APE 1232 and ygcB |
| cas3" | Subtype I-A Subtype I-B | NA | NA | NA | COG2254 | APE1231 and BH0336 |
| cas4 | Subtype I-A Subtype I-B Subtype I-C Subtype I-D Subtype II-B | cas4 and csa1 | NA | NA | COG1468 | APE1239 and BH0340 |
| cas5 | Subtype I-A Subtype I-B Subtype I-C Subtype I-E | cas5a, cas5d, cas5e, cas5h, cas5p, cas5t and cmx5 | casD | 3KG4 | COG1688 (RAMP) | APE1234, BH0337, devS and ygcI |
| cas6 | Subtype I-A Subtype I-B Subtype I-D Subtype III-A Subtype III-B | cas6 and cmx6 | NA | 3I4H | COG1583 and COG5551 (RAMP) | PF1131 and slr7014 |
| cas6e | Subtype I-E | cse3 | casE | 1WJ9 | (RAMP) | ygcH |
| cas6f | Subtype I-F | csy4 | NA | 2XLJ | (RAMP) | y1727 |
| cas7 | Subtype I-A Subtype I-B Subtype I-C Subtype I-E | csa2, csd2, cse4, csh2, csp1 and cst2 | casC | NA | COG1857 and COG3649 (RAMP) | devR and ygcJ |
| cas8a1 | Subtype I-A‡‡ | cmx1, cst1, csx8, csx13 and CXXC-CXXC | NA | NA | BH0338-like | LA3191§§ and PG2018§§ |
| cas8a2 | Subtype I-A‡‡ | csa4 and csx9 | NA | NA | PH0918 | AF0070, AF1873, MJ0385, PF0637, PH0918 and SSO1401 |
| cas8b | Subtype I-B‡‡ | csh1 and TM1802 | NA | NA | BH0338-like | MTH1090 and TM1802 |
| cas8c | Subtype I-C‡‡ | csd1 and csp2 | NA | NA | BH0338-like | BH0338 |
| cas9 | Type II‡‡ | csn1 and csx12 | NA | NA | COG3513 | FTN_0757 and SPy1046 |

TABLE Y-continued

CRISPR enzymes (Cas proteins or Cas-like proteins) organized by Family

| Proposed gene name‡ | System type or subtype | Name from Haft et al.§ | Name from Brouns et al.§ | Structure of encoded protein (PDB accessions)¶ | Families (and superfamily) of encoded protein#** | Representatives |
|---|---|---|---|---|---|---|
| cas10 | Type III^M | cmr2, csm1 and csx11 | NA | NA | COG1353 | MTH326, Rv2823c§§ and TM1794§§ |
| cas10d | Subtype I-D‡‡ | csc3 | NA | NA | COG1353 | slr7011 |
| csy1 | Subtype I-F‡‡ | csy1 | NA | NA | y1724-like | y1724 |
| csy2 | Subtype I-F | csy2 | NA | NA | (RAMP) | y1725 |
| csy3 | Subtype I-F | csy3 | NA | NA | (RAMP) | y1726 |
| cse1 | Subtype I-E‡‡ | cse1 | casA | NA | YgcL-like | ygcL |
| cse2 | Subtype I-E | cse2 | casB | 2ZCA | YgcK-like | ygcK |
| csc1 | Subtype I-D | csc1 | NA | NA | alr1563-like (RAMP) | alr1563 |
| csc2 | Subtype I-D | csc1 and csc2 | NA | NA | COG1337 (RAMP) | slr7012 |
| csa5 | Subtype I-A | csa5 | NA | NA | AF1870 | AF1870, MJ0380, PF0643 and SSO1398 |
| csn2 | Subtype II-A | csn2 | NA | NA | SPy1049-like | SPy1049 |
| csm2 | Subtype III-A‡‡ | csm2 | NA | NA | COG1421 | MTH1081 and SERP2460 |
| csm3 | Subtype III-A | csc2 and csm3 | NA | NA | COG1337 (RAMP) | MTH1080 and SERP2459 |
| csm4 | Subtype III-A | csm4 | NA | NA | COG1567 (RAMP) | MTH1079 and SERP2458 |
| csm5 | Subtype III-A | csm5 | NA | NA | COG1332 (RAMP) | MTH1078 and SERP2457 |
| csm6 | Subtype III-A | APE2256 and csm6 | NA | 2WTE | COG1517 | APE2256 and SSO1445 |
| cmr1 | Subtype III-B | cmr1 | NA | NA | COG1367 (RAMP) | PF1130 |
| cmr3 | Subtype III-B | cmr3 | NA | NA | COG1769 (RAMP) | PF1128 |
| cmr4 | Subtype III-B | cmr4 | NA | NA | COG1336 (RAMP) | PF1126 |
| cmr5 | Subtype III-B‡‡ | cmr5 | NA | 2ZOP and 2OEB | COG3337 | MTH324 and PF1125 |
| cmr6 | Subtype III-B | cmr6 | NA | NA | COG1604 (RAMP) | PF1124 |
| csb1 | Subtype I-U | GSU0053 | NA | NA | (RAMP) | Balac_1306 and GSU0053 |
| csb2 | Subtype I-U§§ | NA | NA | NA | (RAMP) | Balac_1305 and GSU0054 |
| csb3 | Subtype I-U | NA | NA | NA | (RAMP) | Balac_1303§§ |
| csx17 | Subtype I-U | NA | NA | NA | NA | Btus_2683 |
| csx14 | Subtype I-U | NA | NA | NA | NA | GSU0052 |
| csx10 | Subtype I-U | csx10 | NA | NA | (RAMP) | Caur_2274 |
| csx16 | Subtype III-U | VVA1548 | NA | NA | NA | VVA1548 |
| csaX | Subtype III-U | csaX | NA | NA | NA | SSO1438 |
| csx3 | Subtype III-U | csx3 | NA | NA | NA | AF1864 |
| csx1 | Subtype III-U | csa3, csx1, csx2, DXTHG, NE0113 and TIGR02710 | NA | 1XMX and 2I71 | COG1517 and COG4006 | MJ1666, NE0113, PF1127 and TM1812 |
| csx15 | Unknown | NA | NA | NA | TTE2665 | TTE2665 |

The invention claimed is:

1. A composition comprising an isolated extraembryonic endodermal (XEN) cell;
   wherein the isolated XEN cell is a porcine cell; and
   wherein the isolated XEN cell comprises a phenotype of CDX2−, NANOG−, SOX2−, GATA4+, FOXA2+, GATA6+, SALL4+ and SOX17+.

2. The composition of claim 1, wherein the isolated XEN cell is derived from a blastocyst outgrowth, wherein the blastocyst outgrowth was cultured for a duration of about 4 days to about 6 days.

3. The composition of claim 1, wherein the isolated XEN cell is derived from an epiblast.

4. The composition of claim 1, wherein the isolated XEN cell comprises a genetic modification.

5. The composition of claim 1, wherein the composition is free or substantially free of one or a combination of: (i) embryonic epiblastic cells; (ii) cells from a fetus of an animal; and (iii) trophoblastic cells.

6. A library comprising at least two different isolated cell lines, wherein one of the at least two isolated cell lines is an extraembryonic endodermal (XEN) cell line, wherein the XEN cell line is a porcine cell line and wherein the XEN cell line comprises a phenotype of CDX2−, NANOG−, SOX2−, GATA4+, FOXA2+, GATA6+, SALL4+ and SOX17+.

7. The library of claim 6, wherein each of the at least two different isolated cell lines has a different genetic modification.

8. The composition of claim 1, wherein the isolated XEN cell is in culture for at least about 5 days.

9. The composition of claim 1, wherein the isolated XEN cell is passaged greater than 40 times.

10. The composition of claim 4 wherein the genetic modification is a knock-in, knock-out, point mutation or deletion.

11. The composition of claim 1, wherein the isolated XEN cell further comprises a phenotype of EOMES+.

* * * * *

SEQUENCE LISTING

<160> NUMBER OF SEQ ID NOS: 2

<210> SEQ ID NO 1
<211> LENGTH: 2920
<212> TYPE: DNA
<213> ORGANISM: Artificial Sequence
<220> FEATURE:
<223> OTHER INFORMATION: GFP construct

<400> SEQUENCE: 1

```
cctagtcaga ttcgttaact actgggccat gacgggaaca cccctctctc cccctcctta      60
acttggtccc ctctggggct taatctctgg cctgtcctcc caaaggagca tcagatgtga     120
gacttggtgt ggctcggggg tggggggcag gggcggggg gagccaggct gccttgtttg     180
tagccacctg gggaaaataa acaagctgtg gctgcttcgt ggcctgctaa gctctctagg     240
acttgtgcag ggactaagct aagccagtga cactaagctc agcaagggtt tcaggctgca     300
caagtgtcct gtggggacct caaccctgtc tctaagaatc tcacccgaaa ggctcaagga     360
gctgggcatt cagagtcctg catcccaccc cttctcctta cgggagtagt gccccaactg     420
gggtaacctt tgagttctct cagttggggg cgtaggctcg agggcctccg cgccgggttt     480
tggcgcctcc cgcgggcgcc cccctcctca cggcgagcgc tgccacgtca gacgaagggc     540
gcagcgagcg tcctgatcct tccgcccgga cgctcaggac agcggcccgc tgctcataag     600
actcggcctt agaaccccag tatcagcaga aggacatttt aggacgggac ttgggtgact     660
ctagggcact ggttttcttt ccagagagcg gaacaggcga ggaaaagtag tcccttctcg     720
gcgattctgc ggagggatct ccgtggggcg gtgaacgccg atgattatat aaggacgcgc     780
cgggtgtggc acagctagtt ccgtcgcagc cgggatttgg gtcgcagttc ttgtttgtgg     840
atcgctgtga tcgtcacttg gtgagtagcg ggctgctggg ctggccgggg ctttcgtggc     900
cgccgggccg ctcggtggga cggaggcgtg tggagagacc gccaagggct gtagtctggg     960
tccgcgagca aggttgccct gaactggggg ttgggggag cgcagcaaaa tggcggctgt    1020
tcccgagtct tgaatggaag acgcttgtga ggcgggctgt gaggtcgttg aaacaaggtg    1080
gggggcatgg tgggcggcaa gaacccaagg tcttgaggcc ttcgctaatg cgggaaagct    1140
cttattcggg tgagatgggc tggggcacca tctggggacc ctgacgtgaa gtttgtcact    1200
gactggagaa ctcggtttgt cgtctgttgc ggggcggca gttatggcgg tgccgttggg    1260
cagtgcaccc gtacctttgg gagcgcgcgc cctcgtcgtg tcgtgacgtc acccgttctg    1320
ttggcttata atgcagggtg gggccacctg ccggtaggtg tgcggtaggc ttttctccgt    1380
cgcaggacgc agggttcggg cctagggtag gctctcctga atcgacaggc gccggacctc    1440
tggtgagggg agggataagt gaggcgtcag tttctctggt cggttttatg tacctatctt    1500
cttaagtagc tgaagctccg gttttgaact atgcgctcgg ggttggcgag tgtgttttgt    1560
gaagtttttt aggcaccttt tgaaatgtaa tcatttgggt caatatgtaa ttttcagtgt    1620
tagactagta aattgtccgc taaattctgg ccgttttggg ctttttttgtt agacggatcc    1680
atgaattcgc caccatggtg agcaagggcg aggagctgtt caccggggtg gtgcccatcc    1740
tggtcgagct ggacggcgac gtgaacggcc acaagttcag cgtgtccggc gagggcgagg    1800
gcgatgccac ctacggcaag ctgaccctga agttcatctg caccaccggc aagctgcccg    1860
tgccctggcc cacccgtgtg accaccctga cctacgcgt gcagtgcttc agccgctacc    1920
ccgaccacat gaagcagcac gacttcttca gtccgccat gcccgaaggc tacgtccagg    1980
agcgcaccat cttcttcaag gacgacggca actacaagac ccgcgccgag gtgaagttcg    2040
agggcgacac cctggtgaac cgcatcgagc tgaagggcat cgacttcaag gaggacggca    2100
acatcctggg gcacaagctg gagtacaact acaacagcca caacgtctat atcatggccg    2160
acaagcagaa gaacggcatc aaggtgaact tcaagatccg ccacaacatc gaggacggca    2220
gcgtgcagct cgccgaccac taccagcaga acaccccat cggcgacggc cccgtgctgc    2280
```

```
tgcccgacaa ccactacctg agcacccagt ccgccctgag caaagacccc aacgagaagc    2340
gcgatcacat ggtcctgctg gagttcgtga ccgccgccgg gatcactcac ggcatggacg    2400
agctgtacag gcgtaatacg actcactata gggagcgtac gttttgtctg gtcaaccacc    2460
gcggtctcag tggtgtacgg tacaaacctc gaggctggtc tccctcccta cacaatttac    2520 aaagggctc tggggacctg gatgggtaag aaccgggatg tcctgcttcc agaagccctc    2580
agccttccag aaggcattat ggaggggac acaccaggtc tgaatccaag ctctgccatg    2640
tgcttgctgt gtgaccttgg gtaagtcact cattctctcc gggcctcagt gaccttgtct    2700
gtaaaatggg aataatgatt ccatttcctc ttgctgtgca gggcatgtga gggcacatac    2760
aggcccttct ctcttacgtc cggagaattt gagaaatggc aaaatgccga gtgcaaaggg    2820
gaggttggcg gccccctggct gccgctgagg gtcccacaag gcggaggggg agacagggag    2880
gcgatgacag ctgggagagg ggctgccgag cggccgctta                          2920

<210> SEQ ID NO 2
<211> LENGTH: 20
<212> TYPE: DNA
<213> ORGANISM: Artificial Sequence
<220> FEATURE:
<223> OTHER INFORMATION: Col1A sgRNA spacer sequence

<400> SEQUENCE: 2
gagggagacc agcctcgata                                                  20
```